United States Patent
Escutia et al.

(10) Patent No.: US 8,372,015 B2
(45) Date of Patent: Feb. 12, 2013

(54) BODY FLUID SAMPLING DEVICE WITH PIVOTABLE CATALYST MEMBER

(75) Inventors: Raul Escutia, Palo Alto, CA (US); Jeffrey L. Emery, Redwood City, CA (US); Craig M. Litherland, Cupertino, CA (US); Jeffrey M. Jones, Sunnyvale, CA (US); Gregory C. Loney, Los Altos, CA (US); Michael F. Tomasco, Los Altos, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 0 days.

(21) Appl. No.: 11/510,784

(22) Filed: Aug. 28, 2006

(65) Prior Publication Data

US 2008/0077048 A1 Mar. 27, 2008

(51) Int. Cl.
  *A61B 5/00* (2006.01)
  *A61B 17/14* (2006.01)
  *A61B 17/32* (2006.01)
  *A61B 17/00* (2006.01)
  *B65D 81/00* (2006.01)

(52) U.S. Cl. ........ 600/583; 600/578; 600/579; 606/181; 606/202

(58) Field of Classification Search .......... 600/573, 600/575, 583, 576, 578, 579; 606/181–183, 606/201–202
See application file for complete search history.

(56) References Cited

U.S. PATENT DOCUMENTS

| | | | | |
|---|---|---|---|---|
| 3,310,002 A | * | 3/1967 | Wilburn | 73/864.15 |
| 3,626,929 A | * | 12/1971 | Sanz et al. | 600/583 |
| 4,429,700 A | * | 2/1984 | Thees et al. | 600/494 |
| 5,218,966 A | * | 6/1993 | Yamasawa | 600/490 |
| 5,275,159 A | | 1/1994 | Griebel | |
| 6,063,039 A | * | 5/2000 | Cunningham et al. | 600/573 |
| 6,571,114 B1 | | 5/2003 | Koike et al. | |
| 6,679,852 B1 | | 1/2004 | Schmelzeisen-Redeker et al. | |
| 6,706,159 B2 | * | 3/2004 | Moerman et al. | 204/403.03 |
| 6,793,633 B2 | | 9/2004 | Douglas et al. | |
| 7,052,652 B2 | | 5/2006 | Zanzucchi et al. | |
| 7,066,890 B1 | | 6/2006 | Lam et al. | |

(Continued)

FOREIGN PATENT DOCUMENTS

| | | | |
|---|---|---|---|
| JP | 09266889 A | * | 10/1997 |
| JP | 09313465 A | * | 12/1997 |

(Continued)

OTHER PUBLICATIONS

Machine translation of Claims and Detailed Description of JP 09-266889A. Produced Dec. 14, 2007. Japanese Patent Office Website. pp. 1-9.*

(Continued)

*Primary Examiner* — Max Hindenburg
*Assistant Examiner* — John Pani
(74) *Attorney, Agent, or Firm* — Morrison & Foerster LLP

(57) ABSTRACT

An integrated monitoring and body fluid sampling device constructed to permit digital as well as alternate-site body fluid sampling and analysis, the device comprising: a housing; at least one skin-penetration member; and a member constructed for the application of circumferential or vacuum pressure to an appendage; wherein the member is detachably or retractably connected to the housing in a manner such that the integrated monitoring and body fluid sampling device can perform digital or alternate-site body fluid sampling and analysis. Additional arrangements and techniques are also described.

39 Claims, 18 Drawing Sheets

U.S. PATENT DOCUMENTS

| | | |
|---|---|---|
| 7,780,610 B2 | 8/2010 | Sonoda et al. |
| 2003/0153844 A1* | 8/2003 | Smith et al. .................... 600/573 |
| 2003/0212344 A1* | 11/2003 | Yuzhakov et al. ............. 600/583 |
| 2004/0030353 A1* | 2/2004 | Schmelzeisen-Redeker et al. ............................ 606/201 |
| 2004/0092995 A1* | 5/2004 | Boecker et al. ................ 600/576 |
| 2004/0098009 A1 | 5/2004 | Boecker et al. |
| 2004/0138588 A1 | 7/2004 | Saikley et al. |
| 2004/0191119 A1 | 9/2004 | Zanzucchi et al. |
| 2004/0238675 A1 | 12/2004 | Banaszkiewicz et al. |
| 2005/0010134 A1 | 1/2005 | Douglas et al. |
| 2005/0096686 A1* | 5/2005 | Allen ............................ 606/181 |
| 2005/0159678 A1* | 7/2005 | Taniike et al. ................. 600/583 |
| 2005/0187532 A1 | 8/2005 | Thurau et al. |
| 2005/0234486 A1 | 10/2005 | Allen et al. |
| 2005/0245844 A1 | 11/2005 | Mace et al. |
| 2005/0277972 A1 | 12/2005 | Wong et al. |
| 2006/0117616 A1 | 6/2006 | Jones et al. |
| 2006/0135873 A1 | 6/2006 | Karo et al. |
| 2006/0189908 A1 | 8/2006 | Kennedy |
| 2007/0083131 A1 | 4/2007 | Escutia et al. |
| 2007/0179404 A1 | 8/2007 | Escutia et al. |
| 2007/0179405 A1 | 8/2007 | Emery et al. |
| 2007/0255302 A1* | 11/2007 | Koeppel et al. ................ 606/182 |

FOREIGN PATENT DOCUMENTS

| | | |
|---|---|---|
| JP | 10-024028 A | 1/1998 |
| JP | 10-24028 A2 | 1/1998 |
| JP | 63305841 A2 | 12/1998 |
| JP | 2001-017404 A | 1/2001 |
| JP | 2001-309905 A | 11/2001 |
| JP | 2002-000588 A | 1/2002 |
| JP | 2002-219155 A | 8/2002 |
| JP | 2004-208727 A | 7/2004 |
| JP | 2005-523065 A | 8/2005 |
| JP | 2005-523065 A5 | 8/2005 |
| JP | 2005-305157 A | 11/2005 |
| WO | WO-03/088834 A1 | 10/2003 |
| WO | 2005/006939 A2 | 1/2005 |

OTHER PUBLICATIONS

Machine translation of Description of Drawings of JP 09-266889A. Produced Dec. 14, 2007. Japanese Patent Office Website. pp. 1-2.*

Machine translation of JP-09313465. Japanese Patent Office. <www.jpo.go.jp/>. Dec. 7, 2008. pp. 1-7.*

* cited by examiner

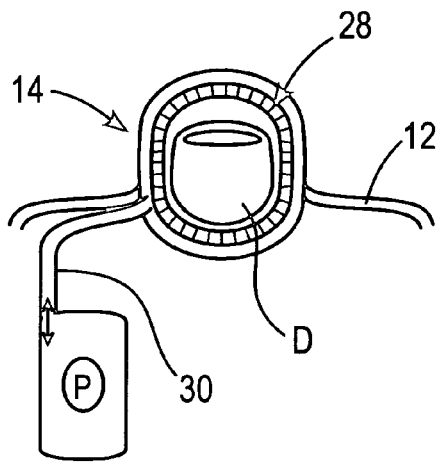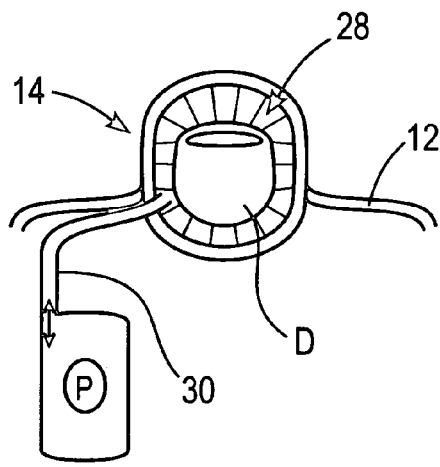
FIG. 3A  FIG. 3B
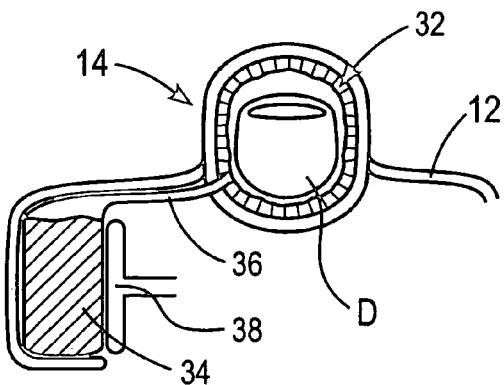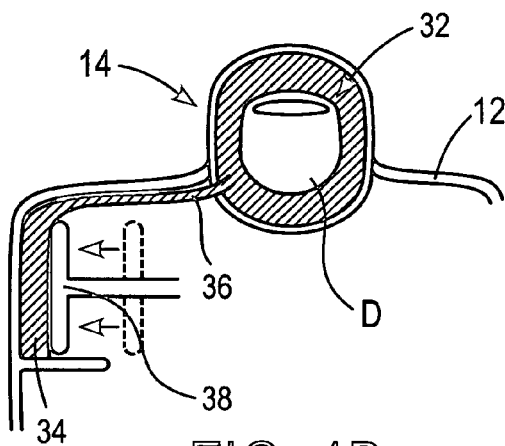
FIG. 4A  FIG. 4B
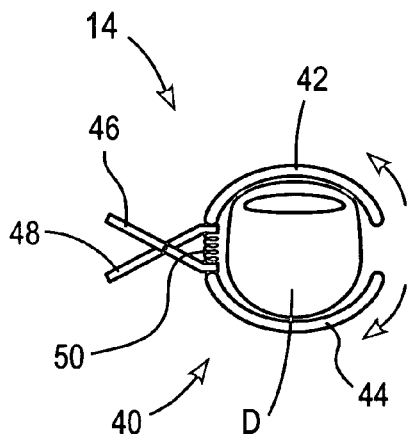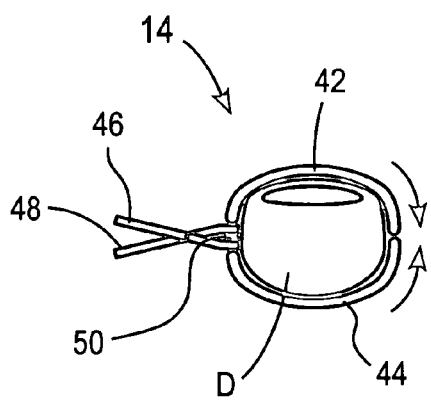
FIG. 5A  FIG. 5B

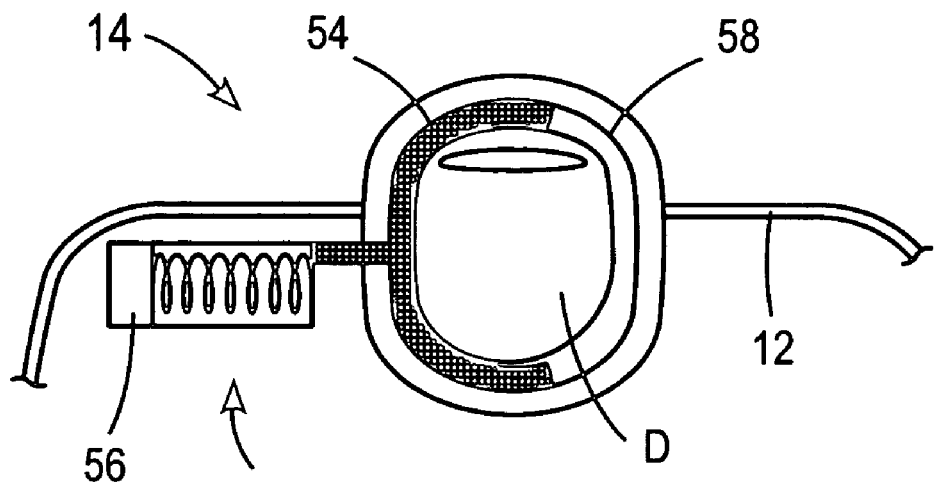
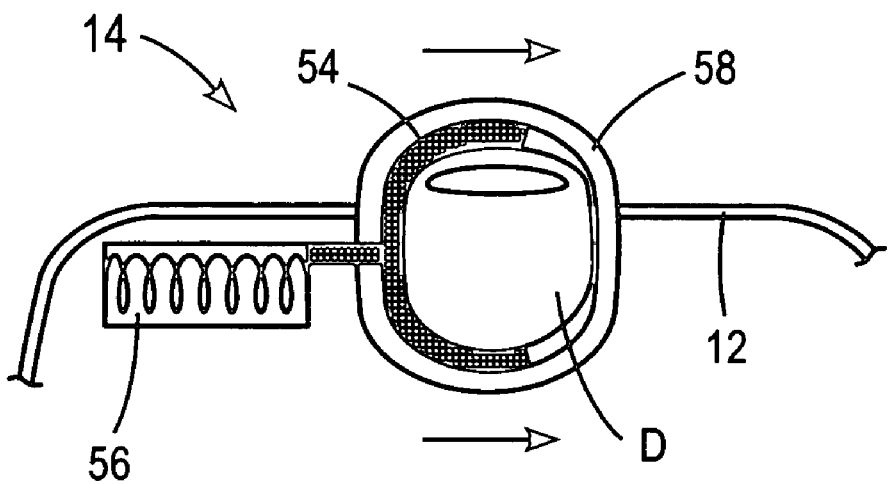

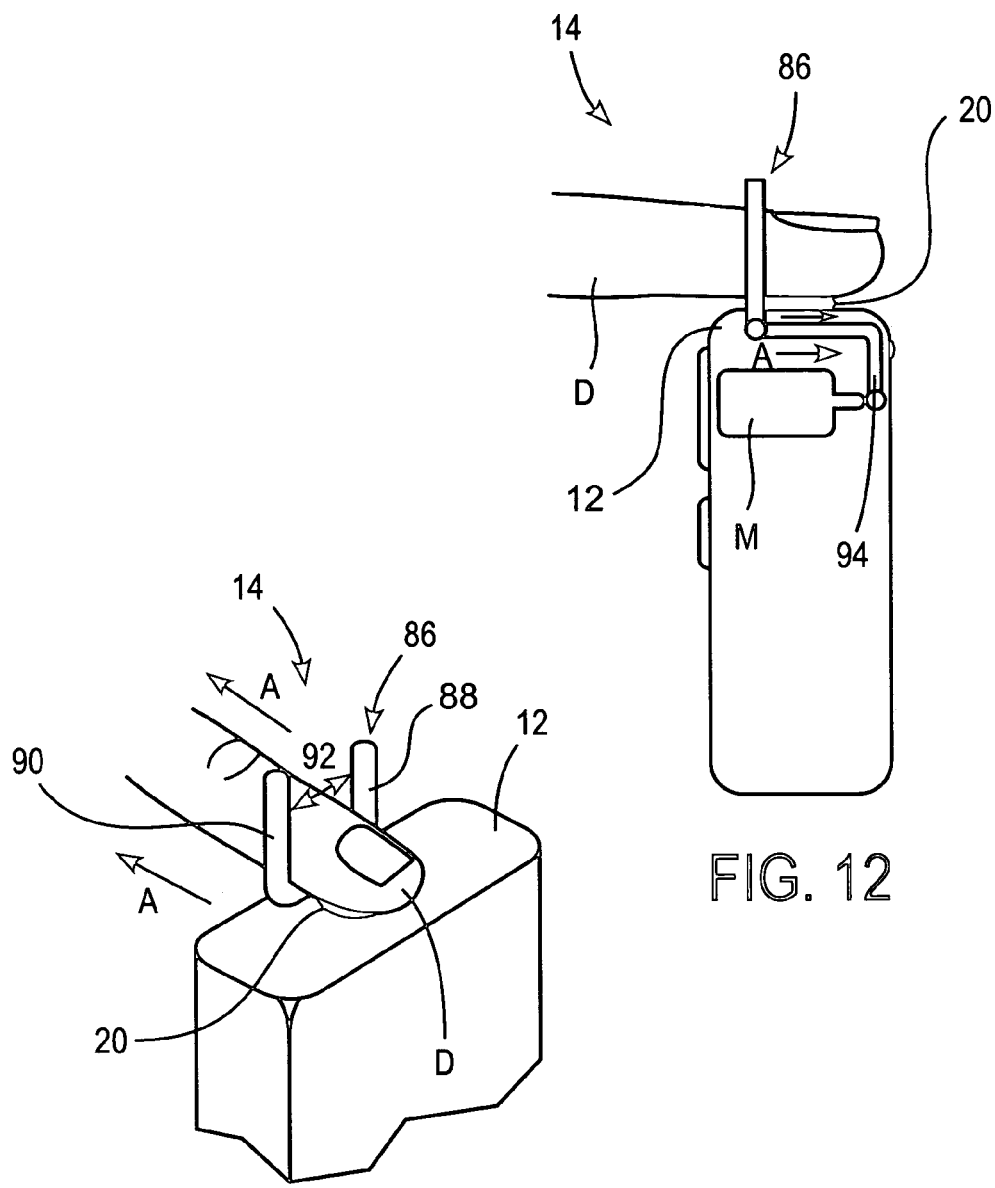
FIG. 12
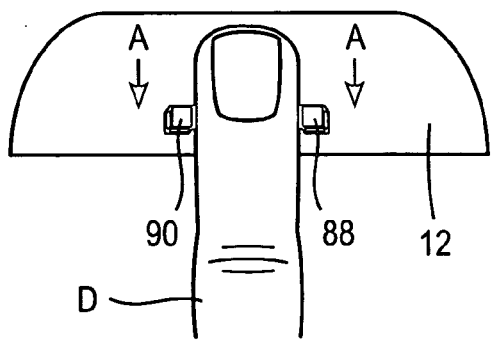
FIG. 11A
FIG. 11B

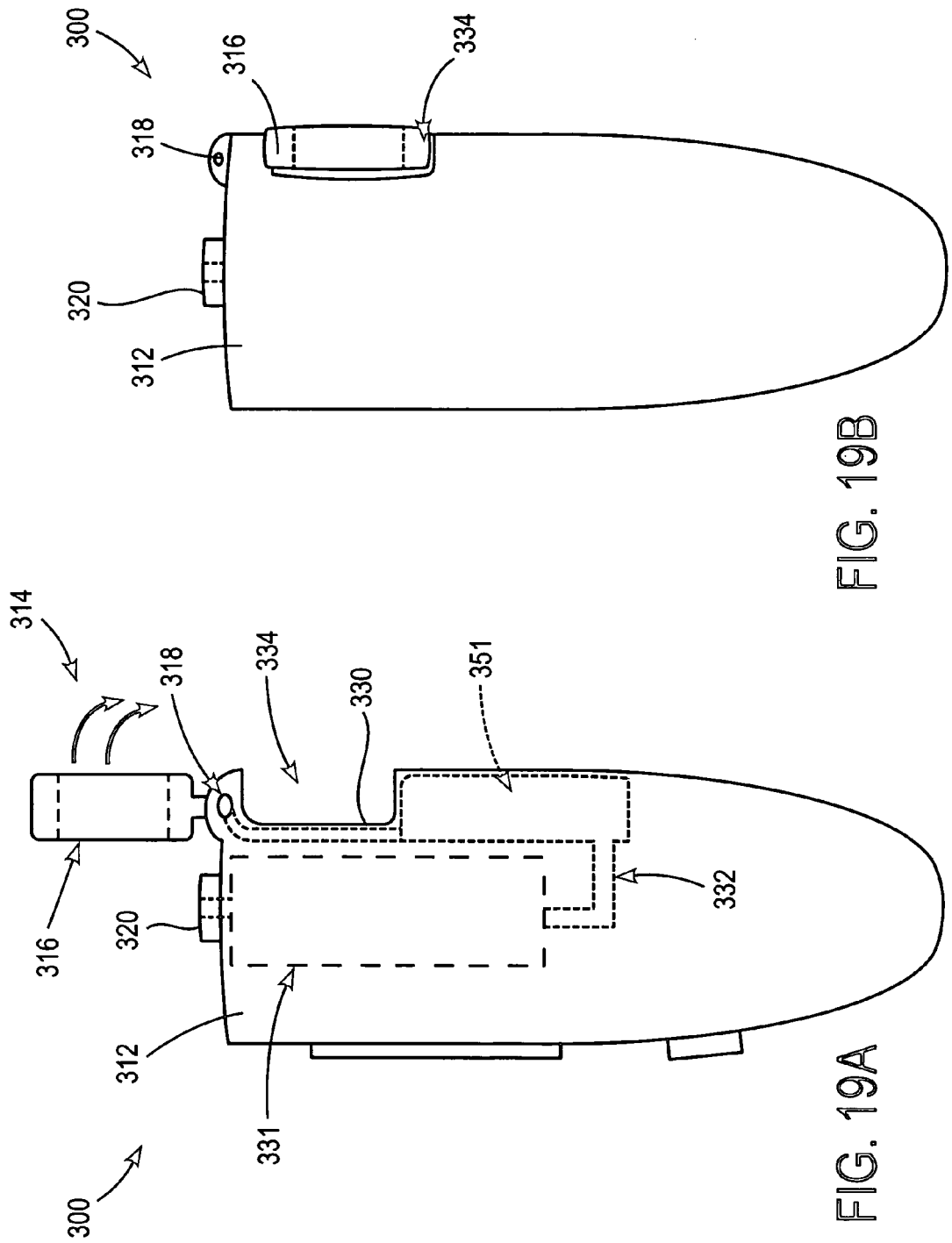

BODY FLUID SAMPLING DEVICE WITH PIVOTABLE CATALYST MEMBER

FIELD OF THE INVENTION

The present invention relates to devices, arrangements and methods involving body fluid sampling with the assistance of a catalyst. In certain embodiments, the present invention is directed to integrated monitoring and body fluid sampling devices and methods that permit both digital and alternative-site body fluid sampling and analysis.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

According to the American Diabetes Association, diabetes is the fifth-deadliest disease in the United States and kills more than 213,000 people a year, the total economic cost of diabetes in 2002 was estimated at over $132 billion dollars, and the risk of developing type I juvenile diabetes is higher than virtually all other chronic childhood diseases.

A critical component in managing diabetes is frequent blood glucose monitoring. Currently, a number of systems exist for self-monitoring by the patient. Most fluid analysis systems, such as systems for analyzing a sample of blood for glucose content, comprise multiple separate components such as separate lancing, transport, and quantification portions. These systems are bulky, and often complicated and confusing for the user. The systems require significant user intervention.

Technology development in the field of self-monitoring of blood glucose has placed the burden of acquiring sufficient blood for conducting a test on the user of the technology. Historically, diabetics have been taught to lance their finger tips to produce blood for conducting the test. Ironically, the fingers are not only one of the most sensitive body parts to pain, but they also are among the areas of skin that are most highly perfused with blood. Earlier versions of consumer-oriented self-monitoring products usually required many microliters of blood, and the finger tips provided a reasonably convenient area to lance that would be most likely to produce the required volume of blood.

More recently, some self-monitoring systems offer the option to the user to test at alternate sites such as the palm, forearm, or thigh. While these sites are generally known to be significantly less sensitive to the pain associated with lancing, the adoption of alternate site testing has been limited for at least four reasons: 1) only a few meter products have been approved by the FDA for testing at alternate sites at this time; 2) many testers do not know that they can use their device at the alternate sites; 3) many testers find it relatively difficult to express sufficient blood at the alternate sites to perform a test; 4) data published in medical literature on some of the meters shows that there is a distinct difference between glucose levels measured at alternate sites relative to the finger, particularly when glucose levels are falling and/or the subject may be hypoglycemic. Consequently, there is a perception by the medical community that there may be an increased risk for delayed or improper treatment by the diabetic if they act only on the basis of glucose levels measured from alternate sites. Thus, the finger lancing site remains the most frequently used test site by far.

Lancing devices and the lancets themselves have also evolved somewhat over the past few decades. Some lancing mechanisms may produce relatively less pain by either 1) projecting the lancet in and out of the skin in a more straight path and thus reducing stimulation of percutaneous nerves which provide the pain stimulus; and 2) offering depth control in the lancing device so that the user may balance the expression of sufficient blood against the level of pain. Furthermore, lancet manufacturers offer a variety of lancet sizes, lengths, and tip bevel patterns with some companies claiming that their lancet is less painful than others.

What remains clear is that the most testers, when lancing at the finger, often must put down the lancing device and apply pressure near the finger tip in order to produce sufficient blood for the test strip in the meter. Many instructions for use with conventional meter systems specifically prescribe that the user perform this "milking" process because without it, many will not spontaneously produce the required volume. Applicants have observed this phenomenon in the use of commonly available commercial sampling and meter systems. When a trained professional lanced the finger tips of 16 volunteer diabetic subjects at the maximum depth setting on commercially available device under controlled conditions, only 15% of lanced sites spontaneously produced sufficient blood for the meter to accurately measure glucose levels.

An engineering model of the lancing wound and of the process for expressing blood to the skin surface provides insight into why the milking process is so often a requisite to successful testing of blood glucose levels. The most commonly recommended site for testing by self-monitoring meter manufacturers is the soft tissue pad on the dorsal side of the distal finger tip. Once a wound is created by the lancing device, a pathway in the soft tissue communicates between the surface of the skin and the damaged blood vessels below the epidermal skin layers. From the perspective of engineering fluid dynamics, this pathway can be considered as a pipe or channel between the reservoir of blood and the surface of the skin.

This pipe, however, often does not remain sufficiently open to permit adequate blood flow largely because of the elastic recoil generated by the extracellular collagen in the skin. Fluid dynamics predicts that a sufficiently large pressure differential must exist across a pipe in order for flow to occur and that the requisite pressure is elevated as the resistance across the pathway increases. In the case of a lanced finger tip, the pressure differential is the pressure of blood below the skin (typically no more than ~20 mmHg) relative to the pressure at the surface of the skin (typically 0 mmHg). For most individuals this low pressure gradient cannot overcome the resistance caused by the tendency of the wound pathway to close.

The manual milking process incorporates two primary biomechanical mechanisms which assist in the expression of blood to the surface of the skin. First, the pressure applied to the soft tissue near the lancing site increases the blood pressure below the skin and elevates the magnitude of the pressure gradient across the wound pathway. This is clearly visible in individuals with lighter colored skin when the finger is compressed near the distal phalangeal joint—the tissue color becomes redder as the capillary bed near the skin surface becomes engorged with blood. With the increased pressure gradient, increased blood flow is expected in rough proportion The second mechanism arises from the deformation of the skin near the lancing site, which may tend to temporarily enlarge the wound pathway with milking. Since the resistance to fluid flow in a simple pipe or channel is proportional to the cross-sectional area of the pathway. Thus, distension of the skin via applied pressure may reduce the wound pathway resistance and enhance blood expression to the skin surface.

Attempts have been made in the past to take steps toward automation of the testing process at alternate sites. Specifically, the Sof-Tact® System offered by Medisense in the early 2000s had the capability to test automatically at alternate sites without any user intervention, but only after each lancet and test strip had been manually loaded into the device. This meter, however, is no longer available on the market.

A device similar to the Soft-Tact device is disclosed in U.S. Patent Application Publication No. 2004/0138588 A1. This device attempts to integrate all the functions required to complete a glucose test into one device. This device however still requires the user to load a lancet and a test strip prior to each individual testing event, and fails to describe a catalyst (i.e. —mechanism to stimulate or enhance expression of blood from the lanced wound site) that ensures that a sufficient sample is expressed from the wound.

This device is described in U.S. Patent Application Publication No. 2005/0010134 A1, and U.S. Pat. No. 6,793,633 B2 uses a spring, or motor driven mechanism to apply pressure around the target wound area. However, the device therein is not a fully integrated system. From the description it appears that the user must insert a new lancet and test strip assembly for each test. Another disadvantage of the device is that the device requires two hands for operation. Specifically, the user must hold the device in one hand while testing a finger on the other hand.

Another disadvantage of the device disclosed above is that for the device to function properly the user must be able to resist the downward force created by the motor/spring driven pressure applications system. In other words, as the device applies a downward force to create pressure around the target site the user must be able to hold the device flush against the skin for it to operate properly. This may present a problem for some elderly or disabled users who may not have the strength to hold the device in place as a test is performed.

Another disadvantage of the device described above is that the devices applies a force via a downward "telescoping" mechanism. A piston-like ring is pressed into the user's skin to aid in sample extraction. This type of pressure catalyst does not trap the maximum amount of blood proximal to the lancing site and thus does not generate a sufficient sample within the target area.

Thus, conventional finger tip sampling devices and methods are overly reliant upon user-dependent milking in order to consistently express a sufficient quantity of blood from the wound site.

Moreover, there is no self-monitoring system currently available that integrates the steps of lancing, expression of body fluid, transport of body fluid to the quantification apparatus, and quantification of the analyte at the finger tip in a fully automatic way. While many diabetics continue to test their blood glucose levels with blood from the finger, testing at the alternate sites offers the advantage of significantly less pain when lancing the palm, forearm, etc. Thus, it would be advantageous to have an automatic and fully integrated meter constructed for testing at both the finger and the alternate sites.

SUMMARY OF THE INVENTION

According to the present invention, there are provided body fluid sampling and monitoring devices and methods that may address one or more of the shortcomings noted above associated with conventional systems and devices. According to the present invention, there may also be provided improved monitoring and body fluid sampling devices and methods that permit both digital and alternative-site body fluid sampling and analysis.

As used herein "digital" means fingers or toes. "Digital body fluid" means expression of body fluid a wound created on the fingers or toes, and encompasses lancing sites on the dorsal or palm side of the distal finger tips.

As used herein "alternate-site" means a location on the body other than the digits, for example, the palm, forearm or thigh. "Alternate-site body fluid sampling" means expression of body fluid from the lancing site on a surface of the body other than the fingers or toes, and encompasses lancing sites on the palm, forearm, and thigh.

As used herein, "body fluid" encompasses whole blood, intestinal fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid.

The current invention may include removable attachments that are specific for either digital or the alternate site testing. The attachments may include a site-specific catalyst to facilitate reliable blood expression. For example, these attachments incorporate either an automatically applied pressure catalyst for the finger, or an automatically applied vacuum catalyst for the alternate site.

Advantages of the present invention may optionally include one or more of the following:

Improved body fluid sampling consistency and reliability when sampling and/or testing at either the digits or an alternative site.

The flexibility of testing at a variety of locations in a variety of orientations with a single integrated meter;

Adoption of this technology being facilitated by the familiarity diabetics have with many lancing devices that are capable of obtaining blood at the finger or alternate site via site-specific interchangeable skin interface components;

It can leverage the same mechanism, e.g., a pump, for generating the catalyst for blood expression at either the digits or alternate sites;

The potential use of interchangeable attachments that are simple, low cost, and easy to manufacture; and Design of the attachment make them easy to use, easy to attach and detach, and easy to clean.

According to certain optional aspects, the primary meter component contains the technology for lancing, transporting, and quantifying the analyte with the blood. The primary meter component may also contain a pump, which facilitates the automatic blood expression via site-specific attachments. For the digits, blood expression may optionally be achieved by directing pressurized air from the pump to a cuff situated at an area proximate to the sampling site. For alternate sites, blood expression may optionally be achieved in the alternate-site attachment by pumping air from and creating a vacuum at the lancing area.

According to one aspect, the present invention is directed to an integrated device, the device comprising: a housing; at least one skin-penetration member; and a member constructed for the application of circumferential or vacuum pressure to a sampling site, wherein the member is detachably or moveably connected to the housing in a manner such that the integrated device can perform digital or alternate-site body fluid sampling and analysis.

According to another aspect, the present invention is directed to an integrated device, the device comprising: a housing; a first footprint and a second footprint disposed on the housing, the first and second footprints constructed to be applied to a sampling site on the skin of a user during body fluid sampling; a plurality of skin-penetration members contained within the housing, a first and second of the plurality of skin penetration members being in registry with the first and second footprint, respectively; and a member constructed for the application of circumferential pressure to the sampling site wherein the first footprint is constructed and arranged for sampling body fluid from a digit, and the second footprint is constructed and arranged for sampling body fluid from an alternate site on the body of the user.

According to a further aspect, the present invention is directed to an integrated device constructed to permit digital as well as alternate-site body fluid sampling and analysis, the device comprising: a housing; at least one skin-penetration member; and a member constructed for the application of circumferential pressure to a digit of the user; wherein the member is movably or retractably connected to the housing in a manner such that the integrated monitoring and body fluid sampling device can perform digital or alternate-site body fluid sampling and analysis.

According to another aspect, the present invention is directed to an arrangement for body fluid sampling, the arrangement comprising: a housing; at least one skin penetration member; and a member constructed to apply circumferential or substantially circumferential pressure to a digit placed therein; wherein the at least one skin penetration member is constructed and arranged to pierce a surface of the skin of the digit at a location proximate to the member constructed to apply circumferential pressure.

BRIEF DESCRIPTION OF THE DRAWING FIGURES

The following description of preferred embodiments can be read in connection with the accompanying drawings in which like numerals designate like elements and in which:

FIGS. 3A-3B are end views of a device constructed according to an alternative embodiment of the present invention.

FIGS. 4A-4B are end views of a device constructed according to a further alternative embodiment of the present invention.

FIGS. 5A-5B are end views of a device constructed according to another alternative embodiment of the present invention.

FIGS. 7A-7B are end views construct according to yet another alternative embodiment of the present invention.

FIGS. 11A-11B are perspective and top views, respectively, of still another embodiment of the device constructed according to the principles of the present invention.

FIG. 12 is a side view of a modified version of the device of FIGS. 11A-11B.

FIGS. 19A-19B are side views of an integrated device formed according to a further alternative embodiment of the present invention.

DETAILED DESCRIPTION

According to a first aspect of the present invention, there are provided arrangements and techniques for reliably expressing body fluid from a digit (e.g., finger or toe). For example, according to the present invention, arrangements and techniques are provided which consistently and reliably express an amount of body fluid from a digit that is sufficient to perform an analysis to quantify the amount of an analyte (e.g., glucose) contained therein.

Figure 1:
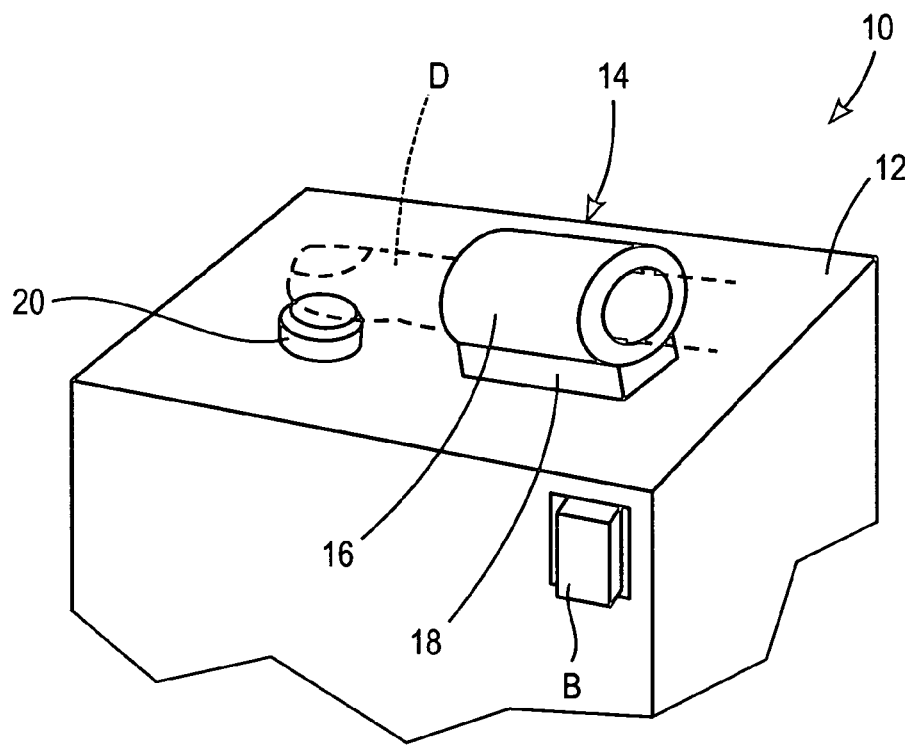
FIG. 1 is a partial perspective view of a device constructed according to the present invention.

One embodiment of an arrangement of the type described above is illustrated in FIGS. 1-2. As illustrated therein, the arrangement 10 may include a housing 12. The housing 12 may have any suitable shape or configuration, and is not limited to the shape and configuration illustrated. The housing can be constructed of any suitable material. For example, the housing may be constructed of a polymeric or metallic material. The arrangement 10 further includes a catalyst device 14. In certain embodiments, the catalyst device 14 is a member for applying pressure to a digit D disposed therein at a location which is proximate to an area of the digit from which a sample of body fluid is to be expressed (i.e., sampling site). The catalyst device 14 may cause the area of the digit from which the sample of body fluid is to be expressed to become perfused with blood and/or body fluid. This effect on the digit facilitates expression of body fluid. According to the illustrated embodiment, the catalyst device 14 comprises an inflatable cuff 16 and a mount 18 that attaches the cuff 16 to the housing 12.

The arrangement 10 further comprises a footprint 20 which is attached to the housing 12. According to the illustrated embodiment, the digit D is placed on the footprint 20 at the sampling site. The footprint 20 is annular in shape according to the illustrated embodiment. However, the footprint is not limited to this shape or configuration. Numerous shapes or configurations may satisfy the function of providing a footprint around the site from which body fluid is to be expressed. According to certain embodiments, the footprint 20 is constructed from a material which facilitates the formation of a seal between the digit D and the footprint 20. For example, suitable materials for this purpose include a relatively soft elastomeric material, such as a silicone rubber.

Figure 2:
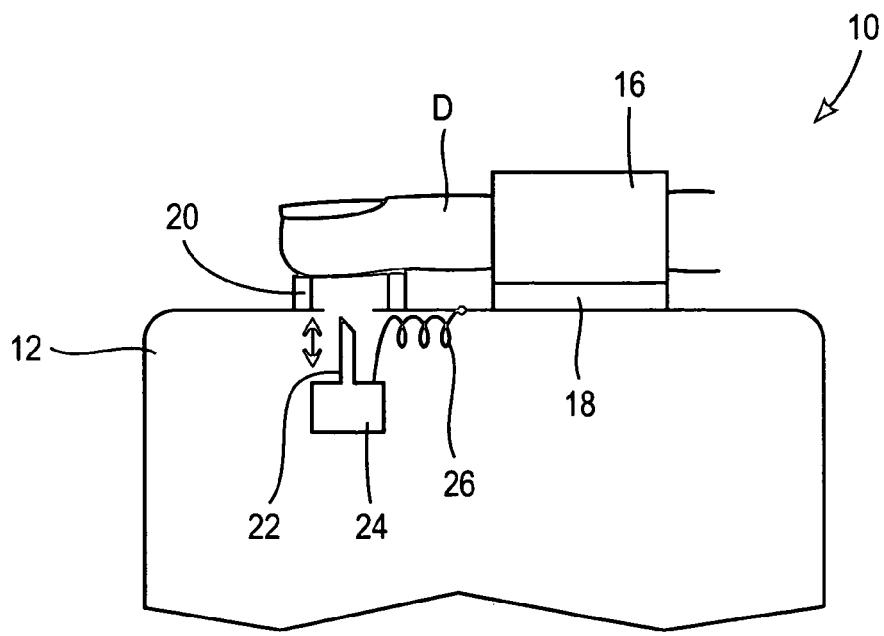
FIG. 2 is a partial cut away side view of the device of FIG. 1.

As illustrated in FIG. 2, the arrangement 10 further includes at least one skin penetration member 22. The at least one skin penetration member 22 can take any suitable form. For example, the at least one skin penetration member can comprise a solid lancet or a hollow needle. The least one skin-penetration member can be formed of any suitable material, such as metal, plastic, glass, etc. Optionally, the at least one skin penetration member can be mounted to a hub 24. In further alternative embodiments, the hub 24 may contain a pad comprising a reagent that changes color upon reaction with a target analyte, as known per se to those skilled in the art. The arrangement 10 can comprise a plurality of skin penetration members 22. According to certain embodiments, the plurality of skin penetration members 22 can be provided in the form of a replaceable cartridge, as will be described in greater detail below. The at least one skin penetration member 22, and/or the hub 24 are attached to an actuation element 26. The actuation element 26 can take any suitable form. For example, the actuation element 26 may comprise a mechanical, electrical or pneumatic element. According to the illustrated embodiment, the actuation element 26 is in the form of a mechanical spring, more specifically, in the form of a torsional spring.

According to certain embodiments of the present invention, the catalyst device 14 operates in an automatic or semi-automatic manner. For example, a user may insert a digit D into the cuff 16 such that the tip region of the digit D is located on the footprint 20. When the user is ready to produce a sample of body fluid, the button B is pressed. This initiates a programmed sequence of events in the device including actuation of the catalyst device 14, thereby applying pressure to the digit D at an area proximate the tip region or sampling site for a predetermined period of time. The skin-penetration member 22 can then be driven into the skin at the tip region of the digit D. At a further predetermined time, the catalyst device 14 is deactivated. This mode of operation can be characterized as "semi-automatic" in that sequence of events must be manually initiated by the user via pressing the button B.

According to one alternative, the mode of operation can be fully automatic. For example, the user inserts a digit D into the cuff 16 and places a tip region thereof on the footprint 20. The arrangement 10 can be provided with one or more sensors that detect and verify that the digit is properly located and ready for the sampling procedure to begin. Once this state has been sensed, the device automatically activates the catalyst 14 which is applied to the digit D for a predetermined period of time. Subsequently, the at least one skin penetration members 22 is driven into the skin of the digit D at a tip region thereof. At a subsequent predetermined time, the catalyst device 14 is deactivated.

The arrangement 10 can form at least part of a device which functions only to sample body fluid. For example, the arrangement 10 can be used to express body fluid from the digit D in the form of a drop of blood which pools on the surface of the skin of the user. This drop of blood can then be transferred to another separate device which then transports and/or analyzes the sample for a target analyte. Alternatively, the arrangement 10 may express a sample of body fluid from the digit D, and then transport the sample to a location which can then be accessed for further analysis by a separate device. For instance, the sample body fluid can be transported to a reagent-containing pad, also contained within the arrangement 10. The sample then reacts with the reagent to produce a detectable spot or signal. The reagent pad can then be analyzed by a separate meter using photochemical, electrochemical, or other suitable techniques known per se to those skilled in the art. The reagent pad can remain within the arrangement 10 during the aforementioned analysis. Alternatively, the reagent pad can be removed from the arrangement 10 and inserted into a separate device, such as an electrochemical or photometric meter.

According to an alternative embodiment, the arrangement 10 forms at least part of an integrated meter. In other words, the arrangement 10 includes additional components which transport the sample, and/or analyze it for content of a target analyte substance. Various examples of such integrated meter will be described in further detail herein.

As alluded to above, the catalyst device 14 can assume many different forms. Exemplary alternative embodiments of the catalyst device 14 will now be described by reference to FIGS. 3A-12.

As illustrated in FIGS. 3A-3B, the catalyst device 14 may comprise an inflatable member or bladder 28 which, when inflated, exerts pressure circumferentially about the digit D. The bladder 28 is connected to a pump P by a supply line 30. The pump P feeds air into the interior of the bladder 28 via the supply line 30 thereby inflating the bladder, as illustrated in FIG. 3B. The supply line 30 may be vented thereby enabling the bladder 28 to be deflated after body fluid has been sampled. Alternatively, the pump P may be reversible, thereby enabling deflation of the bladder 28.

According to another alternative, the catalyst device 14 can comprise an alternative inflatable bladder construction. For example, as depicted in FIGS. 4A-4B, the catalyst device 14 can comprise an inflatable bladder 32 which is connected to a fluid-filled flexible chamber 34 via a feed line 36. The fluid may be noncompressible. The fluid can be forced into the interior of the inflatable bladder 32 by any suitable mechanism. According to the illustrated embodiment, the flexible chamber 34 is compressed by a movable piston 38, thereby forcing the fluid out of the flexible chamber 34 through the feed line 36 and into the interior of the inflatable bladder 32. The piston 38 can be driven by any suitable mechanism or arrangement. For example, the piston 38 can be driven by solenoid, motor, and/or cam arrangement. The specifics of the driving mechanism for the piston 38 being well within the capabilities of those ordinary skill in the art. As with the previously described embodiment of the catalyst device, the embodiment depicted in FIGS. 4A-4B is constructed to exert a circumferential pressure about the digit D.

As illustrated in FIGS. 5A-5B, the catalyst device 14 can comprise a user-controlled spring clip 40. The clip 40 can comprise first and second arms 42,44 that are configured to substantially surround the digit D. According to one alternative, the clip 40 further comprises first and second end portions 46,48 which are graspable by the user. The clip 40 is biased by a spring 50 such that it is closed in its normal state. The user grasps the end portions 46 and 48 pressing them together to open the arms 42,44 of the clip 40 and insert the digit D therein. Then, the user releases the end portions 46,48 and the bias provided by the spring 50 acts to close the arms 42,44 around the inserted digit D. The spring clip 40 thus exerts a circumferential, or substantially circumferential pressure about the digit D.

Figure 6A:
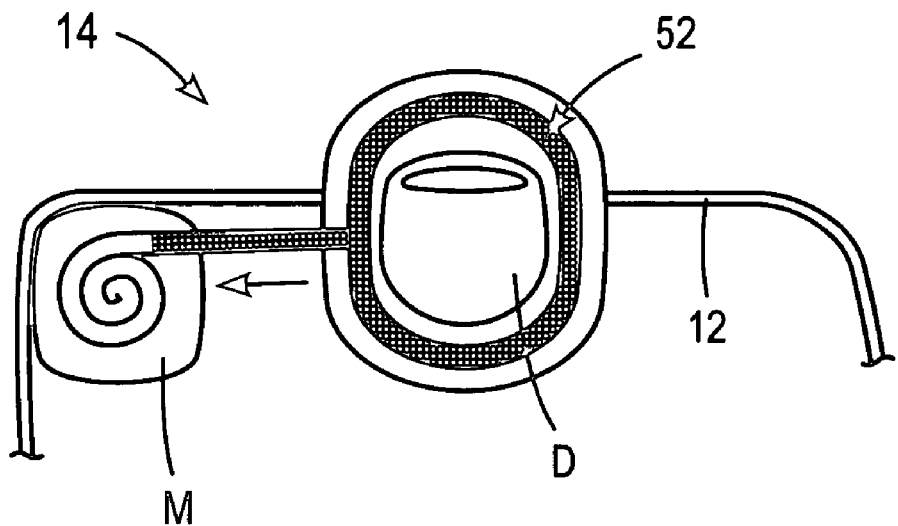
FIGS. 6A-6B are end views of a device constructed according to a further alternative embodiment of present invention.
Figure 6B:
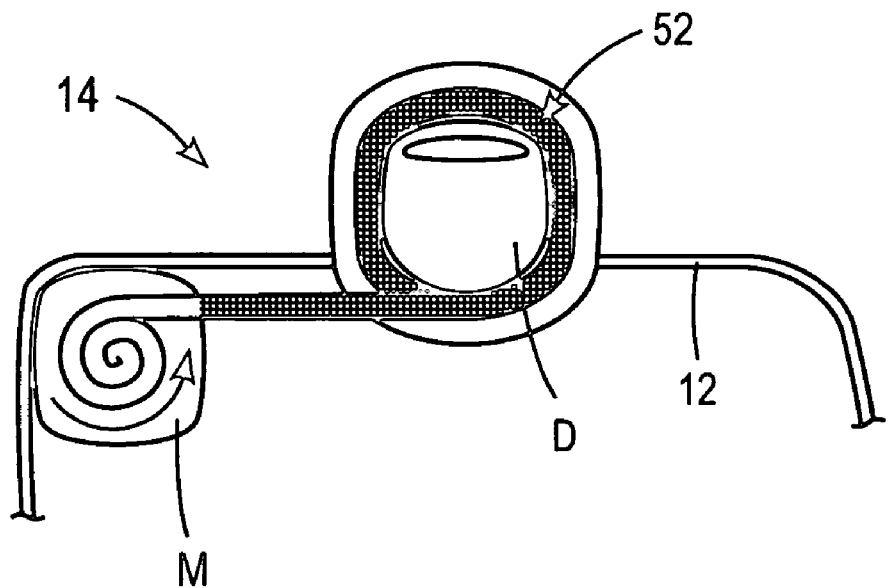

In the alternative construction illustrated in FIGS. 6A-6B, the catalyst device 14 comprises a cable or strap 52 which is attached at one end thereof to a motor M. The motor M is constructed to wind the cable or strap 52 thereby drawing a certain length of the cable or strap 52 about the wound end portion thereof, thus constricting the cable or strap 52 about the digit D. The motor M can be driven by any suitable mechanism, such as a solenoid or spring-loaded mechanism. The specifics of the drive mechanism and the motor M being well within the capabilities of those ordinary skill in the art. Thus, according to this arrangement, circumferential pressure is applied about the digit D.

FIGS. 7A-7B illustrate yet another alternative construction for the catalyst device 14. According to this alternative, a pusher arm 54 brought into contact with the digit D by a pressing member 56 attached to one end thereof. The pressing member 56 can comprise any suitable configuration. For example, the pressing member 56 can be in the form of a compression spring, per the illustrated embodiment. Alternatively, the pressing member 56 can be in the form of the movable fluid or mechanical piston-type arrangement, the specifics of which being well within the capabilities of those ordinary skill in the art. As illustrated in FIG. 7B, the pusher arm 54 is driven into the digit D by the pressing member 56, and in cooperation with a relatively rigid digit housing member 58, creates pressure about the digit D. This pressure is not totally circumferential, but can be characterized as "substantially circumferential."

Figure 8A:
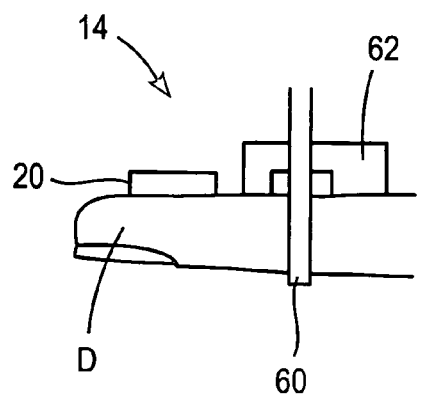
FIGS. 8A-8B are side and perspective views, respectively, of another embodiment of the device constructed according to the principles of the present invention.
Figure 8B:
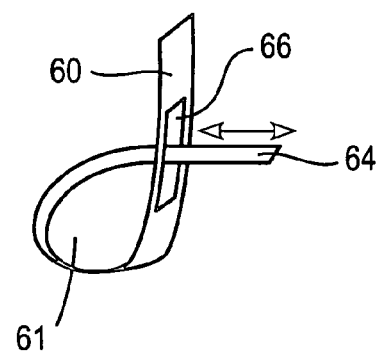

The catalyst device 14 is embodied by a cinchable strap arrangement, as illustrated in FIGS. 8A-8B. As illustrated therein, a strap 60 forms a loop 61 through which a digit D is inserted. The cinchable strap 60 is retained in its operative position with the assistance of a strap housing 62. The strap 60 comprises a free end 64 which passes through an opening or slot 66. In order to cinch the strap about the digit D, the free end 64 is drawn through the slot 66 by a suitable mechanism. Suitable mechanisms include manually pulling the free end 64, or mechanically drawing the free end 64 by suitable arrangements such as a motor, cam, or spring-loaded device of the type previously described herein. The specifics of the drawing mechanism being well within the capabilities of those ordinary skill in the art. The strap 60 is preferably formed from a material which facilitates cleaning thereof any event that body fluid comes into contact with the strap 60 during the sampling procedure. For example, the strap 60 can be formed of a non-porous thermoplastic material to facilitate cleaning. The cinching of the strap about the digit D acts to apply circumferential or substantially circumferential pressure thereto.

Figure 9A:
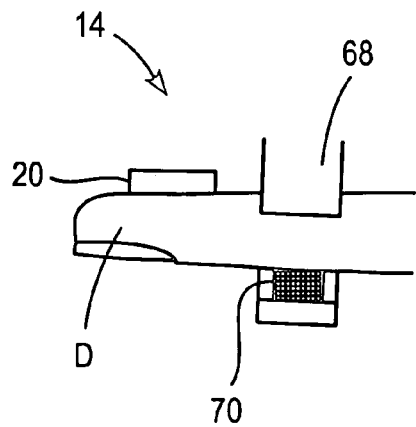
FIGS. 9A-9B are side and end views, respectively, of a further embodiment of a device constructed according to the principles of the present invention.
Figure 9B:
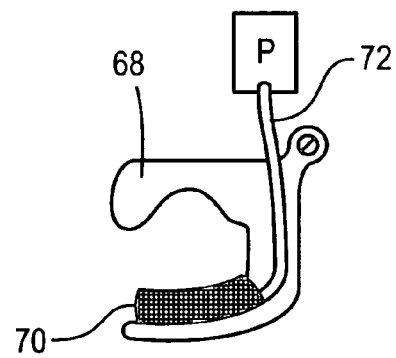

According to a further alternative embodiment, and as illustrated in FIGS. 9A-9B, the catalyst device 14 can comprise an open jaw 68 through which a digit D is inserted. The jaw 68 comprises an interior portion which is roughly shaped correspond to the circumference of the digit D. The dimensions of the interior portion of the jaw 68 are large enough to accommodate most digits therein without significant interference. Disposed within the inner portion of the jaw 68 is an inflatable bladder or pillow 70. The interior of the inflatable pillow 70 is in fluid communication with the pump P through a feed line 72. The pump P is operable to force air into the interior of the inflatable pillow 70 via the feed line 72. The feed line 72 can be vented to permit deflation of the inflatable pillow 70. Alternatively, the pump P can be reversible thereby providing an alternative mechanism for deflating the pillow 70. Thus, once inflated, the digit D is forced with a certain degree of pressure into opposing walls of the interior portion of the jaw 68. Thus, according to this embodiment, substantially circumferential pressure is applied to the digit D, thereby facilitating the expression of body fluid therefrom.

Figure 10A:
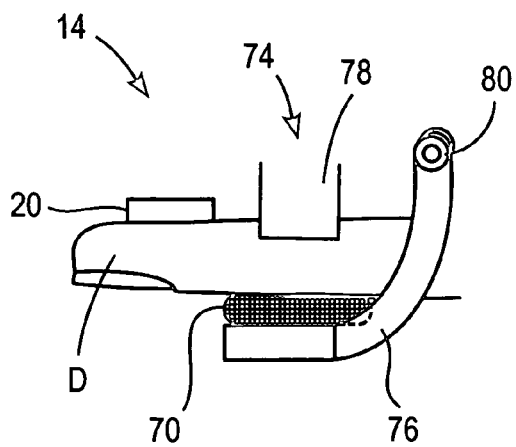
FIGS. 10A-10B are side and end views, respectively, of yet another embodiment of a device constructed according to the principles of the present invention.
Figure 10B:
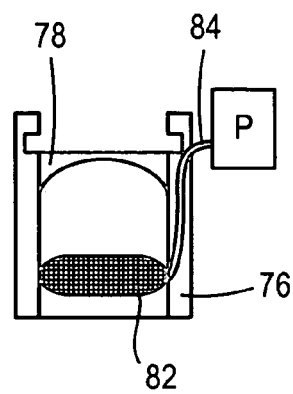

A modified version of the previously-described embodiment as depicted in FIGS. 10A-10B. According to this embodiment, the catalyst device 14 is in the form of what can be described in general as a closed jaw 74. In the illustrated embodiment, the closed jaw 74 comprises a movable arm 76 which is connected to a frame 78 via a spring-loaded hinge 80. The arm 76 can be swung open to permit the introduction of the digit D therein. The hinge is biased to normally close the movable arm 76. An inflatable pillow 82 is disposed on the movable arm 76, and is connected to a pump P by a connection line 84. The connection line 84 can be vented, thereby allowing the pillow 82 to be deflated. Alternatively, the pump P can be reversible, thereby providing an alternative mechanism by which the pillow 82 can be deflated. Once the pillow 82 is inflated, the digit D is forced into opposing surfaces in the interior of the closed jaw 74 thereby creating the desired pressure. The closed nature of the jaw 74 of this particular embodiment can act to provide pressure around a greater degree of the circumference of the digit D as compared to the previously described embodiment.

Yet another possible catalyst device construction is depicted in FIGS. 11A-12. According to this embodiment, the catalyst device is in the form of a U-shaped channel 86 comprising first and second arms 88,90. According to this embodiment, the user places a digit D between the first and second arms 88 and 90, then draws the digit D back in the direction of the arrows A until the tip-region of the digit is properly located for sampling to occur (e.g., disposed upon the footprint 20). According to preferred aspects, the first and second arms 88, 90 are flexible, and the distance 92 between the first and second arms 88, 90 is such that there is a significant amount of interference between the digit D and the first and second arms 88, 90 as the digit D is pulled back through the U-shaped channel 86. This interference creates the desired pressure upon the digit D at a location proximate to the tip region thereof from which to sample body fluid is to be expressed. According to a further modification of the above described embodiment, instead of having the user move the digit D manually through to U-shaped channel, the arrangement can comprise a mechanism for moving the U-shaped channel told to do the digit D. Such a construction as illustrated in FIG. 12. According to this modification, the U-shaped channel is attached to a motor M via an appropriate mechanical linkage 94. The motor M drives the linkage 94, and the attached U-shaped member 86, in the direction of arrow A. Upon reversal of the motor, the linkage 94 and the attached U-shaped member 86 is driven back in the opposite direction. Of course, it should be understood that the driving mechanism is not limited to the illustrated example, and can take on any suitable form. For example, the driving mechanism can comprise a solenoid, spring driven mechanism, or other system known to produce a linear motion. The particulars of the driving mechanism being well within the capabilities of those ordinary skill in the art. Just as the previously described embodiment, the U-shaped member has first and second arms 86,88 with a distance 92 between them which creates an interference with the digit D when moved in the direction of arrow A. The pressure created on the digit D according to these configurations can be described as "substantially" circumferential pressure.

According to a further aspect of the present invention, the above-described catalyst devices (e.g., 14), as previously described herein, can form at least part of an integrated device. As previously noted, as used herein, the term "integrated device" or "integrated meter" means a device or meter that includes all components necessary to perform sampling of the body fluid, transport of the body fluid, quantification of an analyte, and display of the amount of analyte contained in the sample body fluid. Thus, according to the principles of the present invention, an integrated device or meter can comprise one or more, or any combination, of the features previously described herein. According to further aspects of the present invention, and integrated meter or device can comprise additional components and/or features, which are described as follows.

Figure 13:
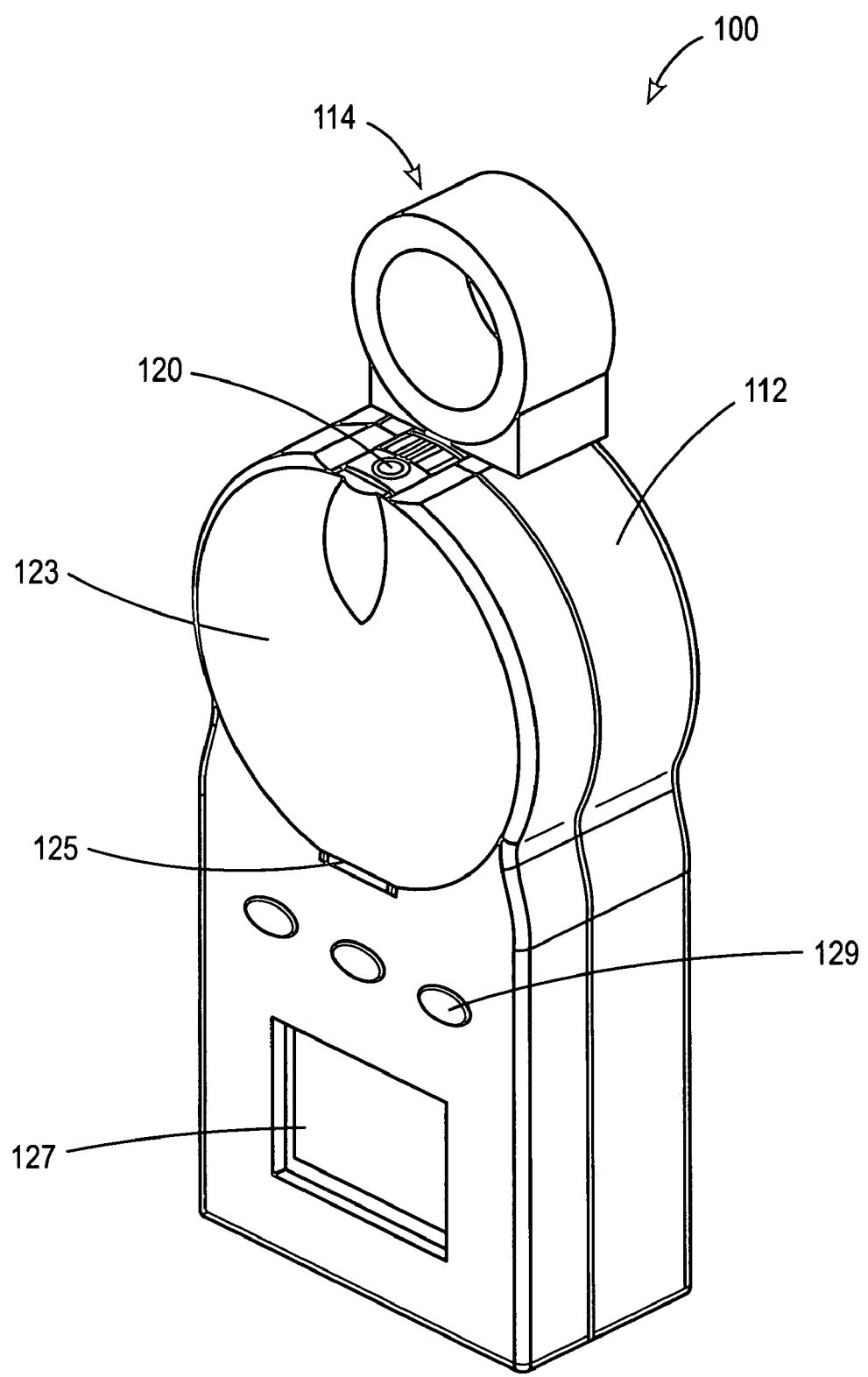
FIG. 13 is a perspective view of an integrated device formed according to one embodiment of the present invention.

One such integrated meter is illustrated in detail in FIGS. 13-17. As illustrated therein, the integrated meter 100 generally comprises a housing 112 and a catalyst device 114. The catalyst device 114 may take any suitable form. For example, as illustrated in FIG. 13, the catalyst device 114 may comprise a cuff 116 attached to the housing 112 via a mount 118. Alternatively, the catalyst device 114 can comprise any of the previously described alternative catalyst device configurations. The integrated meter 100 may further comprise a footprint 120 of the type previously described. A door 123 can be provided on the housing 112. The door 123 is connected via a hinge 125 to the housing 112. As described in further detail below, the door 123 can be opened to reveal a cartridge containing a plurality of skin-piercing elements. In the illustrated embodiment, the integrated meter 100 further includes a display 127 for communicating the results of the analysis on the sample body fluid for the presence and/or concentration of an analyte contained therein. The integrated meter 100 may further include one or more buttons 129 which can be pressed by the user to engage various functions and interfaces of the integrated meter 100.

Figure 14:
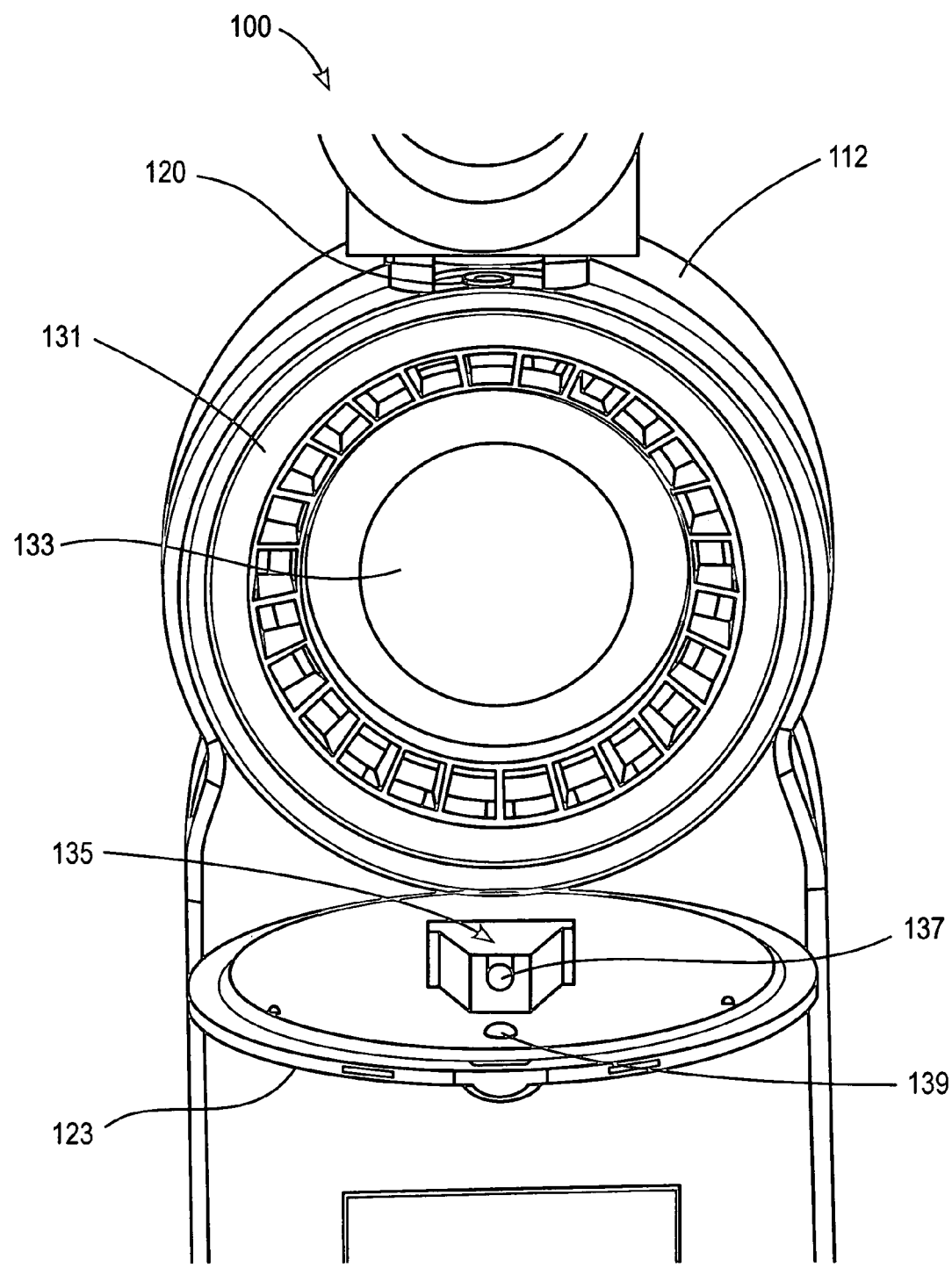
FIG. 14 is a partial side view of the integrated device of FIG. 13.

FIG. 14 is an illustration of the integrated meter 100 with the door 123 opened to reveal further details of the interior components of the integrated meter 100. As illustrated therein, the housing 112 contains a cartridge 131 therein. In the illustrated embodiment, the cartridge 131 is circular and contains a plurality of skin-piercing elements as further described herein. The cartridge 131 is mounted about a hub 133 and is rotatable. Thus, upon sampling a skin-piercing element is driven through an opening in the housing in registry with the footprint 120 and pierces the skin of the user. Once the test has been completed, the cartridge 131 can be rotated such that an unused skin-piercing element now comes into registry with the opening in the housing and the corresponding opening in the footprint 120 in preparation for the next sampling event. It should be understood that the present invention is not limited to the illustrated circular cartridge having the particular configuration depicted in the drawing figures. To the contrary, a number of alternative cartridge configurations are possible, such as a slidable linear or polygonal configuration (not shown). Also illustrated in FIG. 14 is the presence of a light source 139 disposed on the back of the door 123. The light source 139 can take any suitable form, such as a light emitting diode. It should be understood that alternative light sources may also be utilized. The function of the light source 139 will be described in further detail below.

Figure 15:
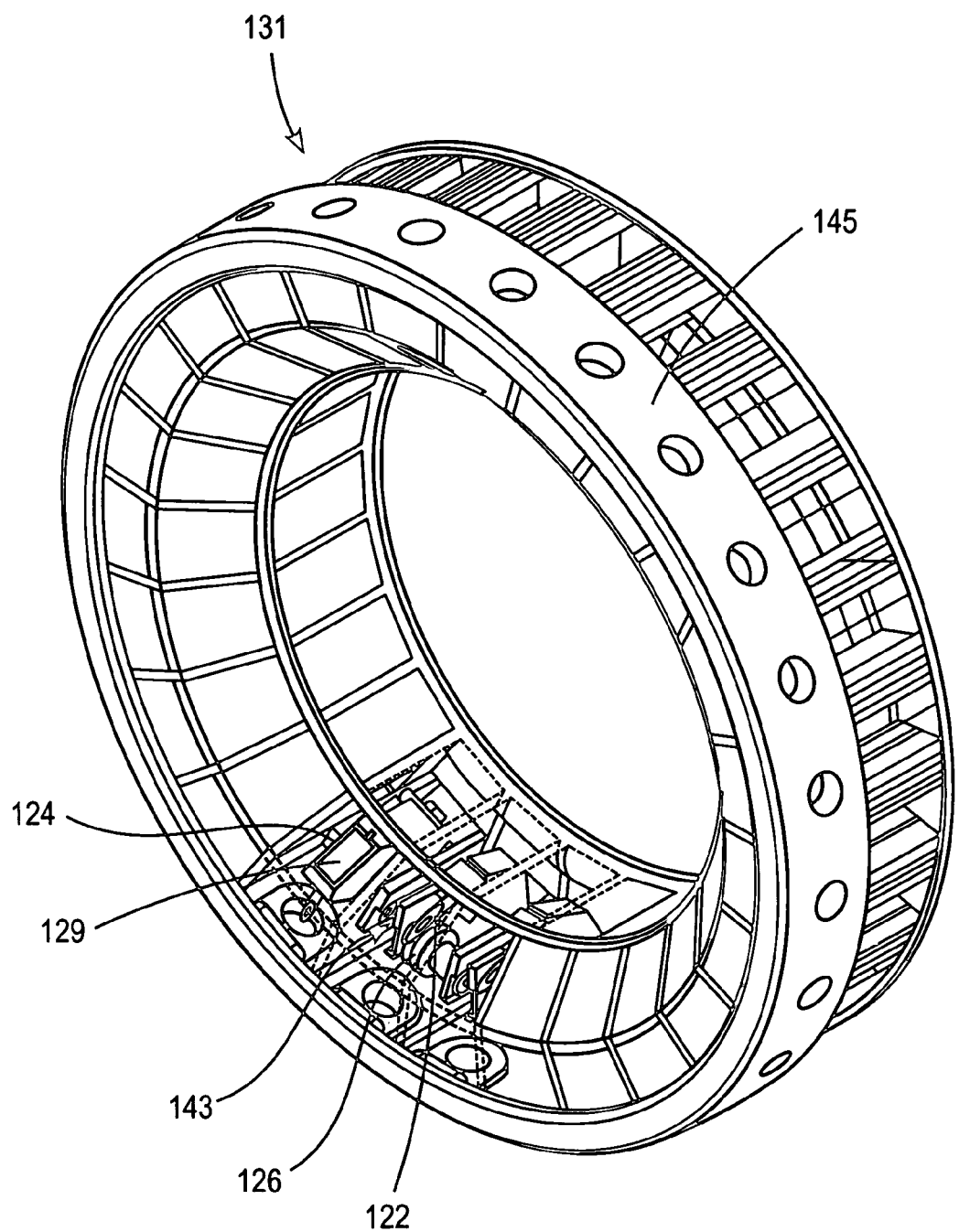
FIG. 15 is a perspective view of a component of the integrated device of FIG. 13.
Figure 16:
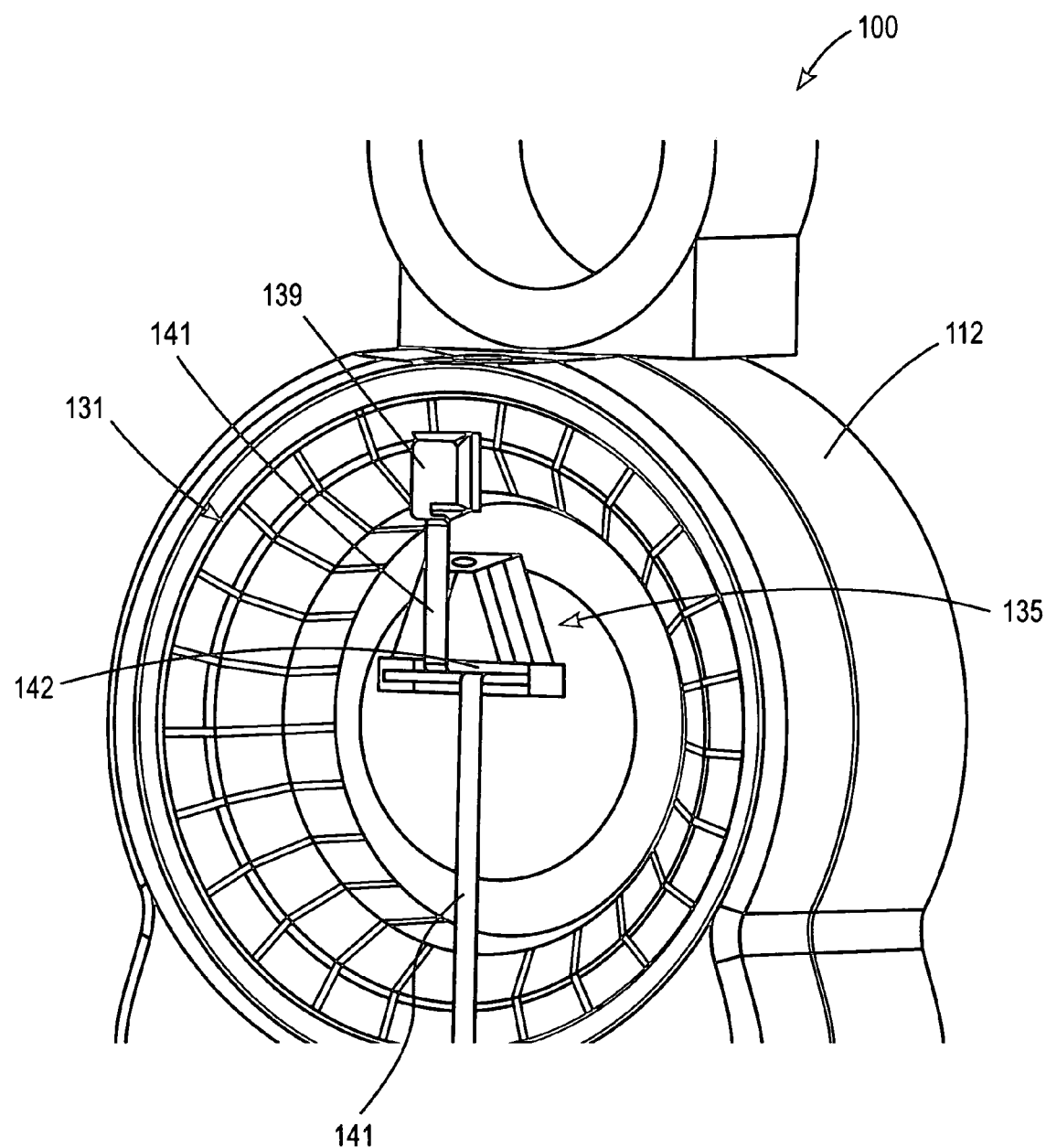
FIG. 16 is a partial perspective view of various components of the integrated device of FIG. 13.

Further details of the optical assembly 135, the light source 139, and the replaceable cartridge 131 are illustrated in FIGS. 15-16. As illustrated therein, the replaceable cartridge 131 generally may comprise a plurality of compartments defining a plurality of body fluid sampling and analysis sites 132. Contained in each sampling and analysis site 132 is a skin penetration member 122. Each skin penetration member 122 can take any suitable form. According to the illustrated embodiment, each skin penetration member 122 is in the form of a hollow needle. It should be understood that alternative skin penetration members may also be utilized consistent with the principles of the present invention (e.g., solid lancets, etc.) each skin-penetration member can be attached to a needle hub 124. Each needle hub 124 is, in turn, attached to an actuation element 126. It should be understood that a number of different actuation elements may be utilized according to the principles of the present invention. The actuation elements can be mechanical, electrical, pneumatic, etc. According to the illustrated embodiment, the actuation element 126 is in the form of a torsional spring. Upon activation, the torsional spring drives the needle hub 124 and the attached skin penetration member 122 into the skin of the user disposed on the footprint 120. According to certain embodiments, each sampling/analysis site 132 further contains a signaling mechanism which produces a detectable signal when contacted with a target analyte contained in a sample of body fluid expressed from the skin of a digit D. A number of suitable mechanisms are envisioned. The mechanisms may be based on conventional technologies such as photometric or electrochemical analysis. According to the illustrated embodiment, each needle hub 124 contains a reagent pad 129 which generally comprises an absorbent material containing a chemical reagent which, upon reaction with a target analyte, produces a chemical reaction that results in a detectable signal. The reagent pad 129 is in fluid communication with the inner bore of the skin piercing element 122. As noted above, the signal can be detected optically, electrochemically, or by other suitable means. According to one embodiment, the reagent pad 129, upon reaction with the target analyte, produces a spot which is optically detected by the optical assembly 135 in a manner known to those skilled in the art. The spot produced by the above-mentioned reaction can be observed optically through a window 143 formed along the interior region of the illustrated cartridge 131 by the optical assembly 135. In this regard, light emitted from the light source 139 is incident upon the reagent pad 129, and reflects off the surface thereof. Upon formation of a reaction spot on the surface of the reagent pad 129, the amount of light reflected off the reaction spot differs from the light reflected off of other portions of the reagent pad 129 containing no such reaction spot. This reflected light is picked up by the optical assembly, first through the lens 137 (FIG. 14), and eventually is incident upon an optical detector element 142 (FIG. 16).

The optical detector element 142 generally comprises one or more detector elements. According to one alternative construction, the detector element 142 comprises a plurality of detector elements formed in an array. The array can take any suitable configuration, and can be a linear array according to one nonlimiting example. The detector elements can comprise any suitable construction. For example, the detector elements 142 can comprise a photo diode, CCD, or CMOS based detector element. The signals transmitted to the detector element 142 are passed on to suitable electronics contained within the housing 112 (see, e.g., FIG. 17) via suitable electrical connectors, such as flexible ribbons 141. The specifics of the electronics and signal interpretation being familiar to those of ordinary skill in the art. While not necessary to enable practice of the presently claimed invention, further details concerning the construction, function and arrangement of the analysis sites 132, and components contained therein, can be gleaned from the disclosure contained in U.S. patent application Ser. No. 60/721,966, entitled DEVICE FOR FLUID ANALYSIS WITH SAMPLE EXTRACTION AND TRANSPORT, the entire content of which is incorporated herein by reference. Similarly, while not necessary to enable practice of the presently claimed invention, further details concerning the structure, function, and arrangement of the optical assembly 135, and the components contained therein, can be gleaned from the disclosure contained in U.S. patent application Ser. No. 11/239,122, entitled ANALYTE DETECTION DEVICES AND METHODS WITH HEMA- TOCRIT/VOLUME CORRECTION AND FEEDBACK CONTROL, the entire content of which is incorporated herein by reference.

Figure 17:
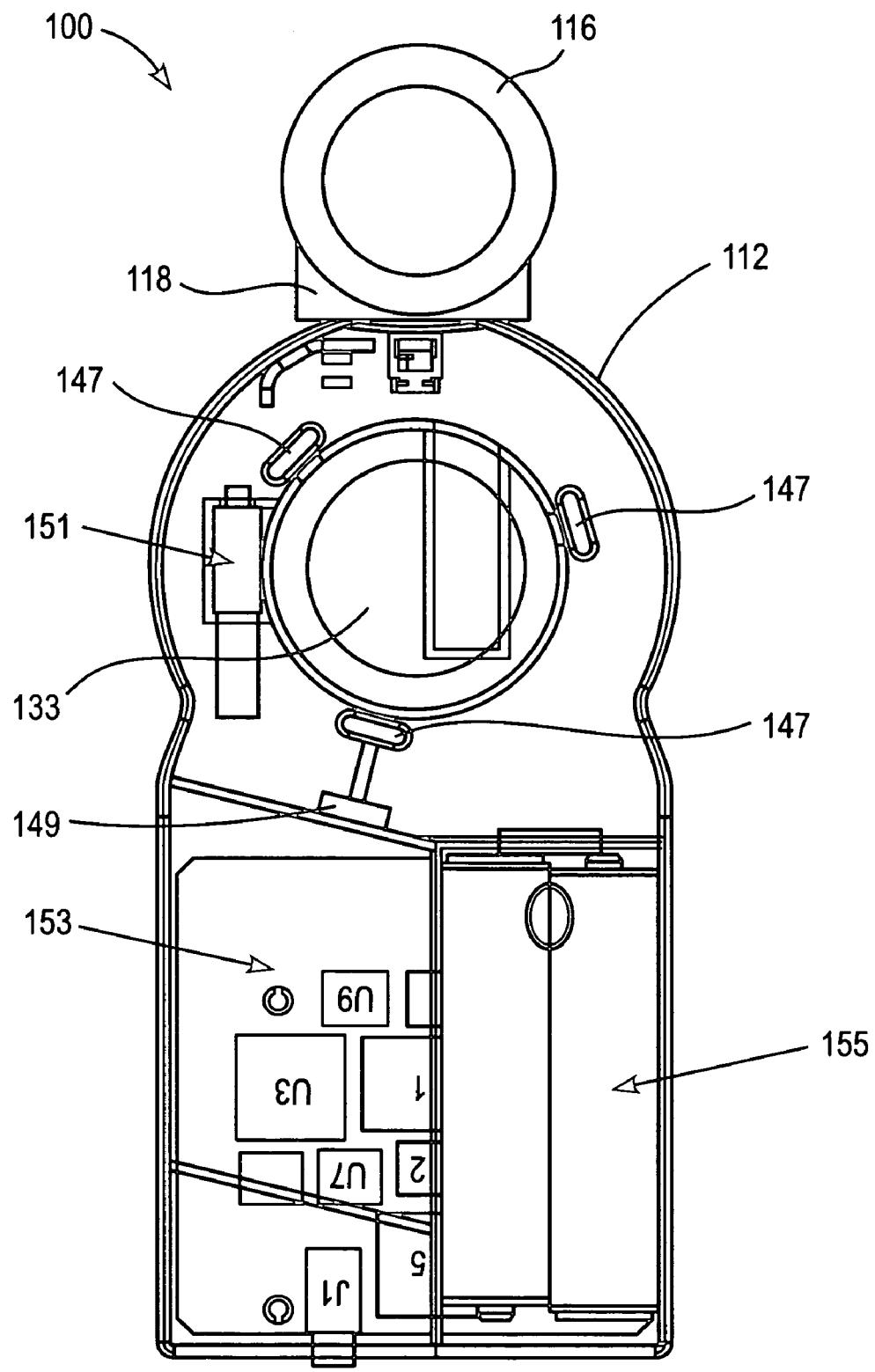
FIG. 17 is a side view illustrating various additional components of the device of FIG. 13.

Additional components of an integrated meter 100 are illustrated in FIG. 17. The view depicted in FIG. 17 is that of an integrated meter 100 with the back panel removed to reveal the above-referenced additional components. For example, as illustrated in FIG. 17, the integrated meter 100 may further include a plurality of rollers 147 which cooperate with the cartridge 131 and a motor drive 149 thereby enabling the rotation of the cartridge 131 about the hub 133, and indexing of the analysis sites 132 with the footprint 120. The integrated meter 100 may also include a pressure pump 151 which, according to certain embodiments, comprises a pump capable of producing both positive and negative pressures. Thus, for example, the pump 151 can create a positive pressure within the cuff 116, as previously discussed. Alternatively, or in addition, the pump 151 can create a negative or vacuum pressure at the surface of the skin located over the footprint 120. The integrated meter 100 may further include appropriate electronics, as embodied in the circuit board 153 of the illustrated embodiment. Preferably, the circuit board contains conventional electronic components capable of controlling the various functions of the integrated meter 100 in the desired manner. The particulars of the circuit board 153, and electronic components disposed thereon, being well-known to those of ordinary skill in the art. Finally, the integrated meter 100 may further comprise a suitable power supply 155, such as the illustrated batteries.

Figure 18:
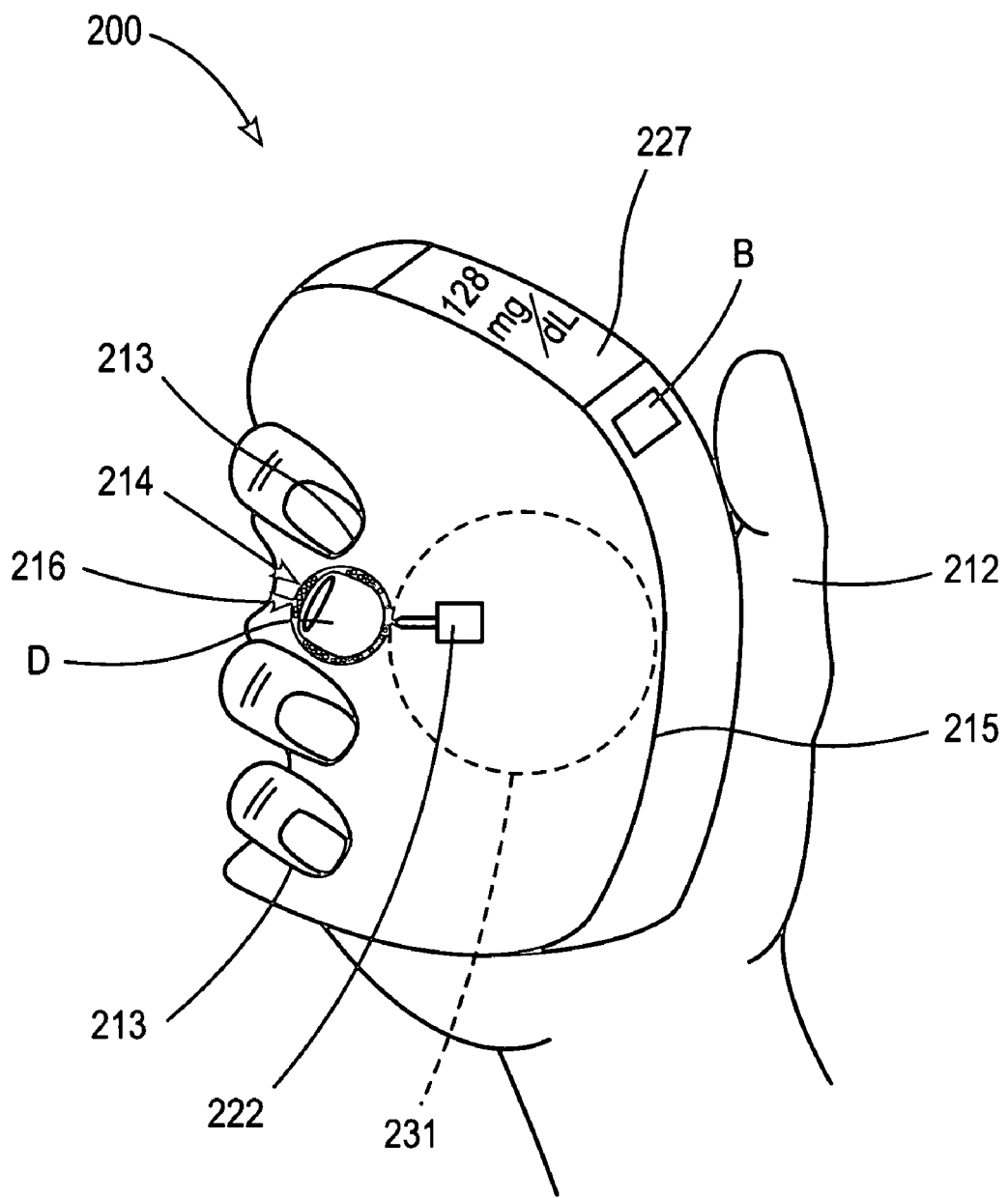
FIG. 18 is a perspective view of an integrated device formed according to an alternative embodiment of the present invention.

The embodiment of the integrated meter 100 illustrated in FIGS. 13-17 includes a catalyst device 114 in the form of the cuff 116 which is fixedly mounted to the housing 112 via mount 118. Due to this construction, the integrated meter 100 is suitable for digital testing (e.g., finger testing). A modified form of the integrated meter 100 is illustrated in FIG. 18. As illustrated therein, the integrated meter 200 comprises a housing 212 which a shaped and contoured to conform to the grip of a user. In this regard, the housing 212 includes a plurality of recesses 213 which are shaped in contoured to be grasped by the fingers, as well as a contoured rear surface 215 which is shaped to conform to surfaces of the palm and thumb of the user. The integrated meter 200 comprises a catalyst device 214 comprising, at least in part, passageway sized and configured to permit the insertion of a digit D therein. The catalyst device 214 can have a construction of any of the types of catalyst device as previously described herein. According to the embodiment that is illustrated in FIG. 18, the catalyst device 214 comprises an inflatable bladder or cuff 216. The cuff 216 is structured and operates in the same manner previously described herein. The integrated meter 200 further comprises a suitable display 227 which communicates the results of the analysis to the user. The integrated meter 200 further contains at least one skin piercing element 222. Optionally, a plurality of skin piercing elements 222 are contained within the housing 212. According to certain embodiments, a plurality of skin piercing elements 222 are provided in the form of the replaceable cartridge 231 having the same construction as the previously described cartridge. As previously described herein, the catalyst device 214 has a mode of operation which can be characterized as automatic, or semi-automatic. For example, the catalyst device 214 can be activated manually by the user by pressing a button B, which initiates the catalyst as well as further operation of the device, as previously described herein. Alternatively, one or more sensors are provided in the integrated meter 200 that function to determine when a digit D is properly positioned and ready for sampling to begin. Upon detection of this state, the catalyst as well as further operations of the device are automatically initiated. The integrated meter 200 may also have any one or combination of features described as being associated with integrated meter 100.

The previously described embodiments illustrated in FIGS. 13-18 are configured for digital body fluid sampling and analysis. According to further aspects of the present invention, modified devices and techniques are provided which permit both digital body fluid sampling and analysis as well as alternate-site body fluid sampling and analysis, which may be performed at the election of the user. In the description that follows, it should be understood that the integrated meters described herein may have any of the features and/or modes of operation as that of the previously described embodiments.

A first illustrative embodiment of an integrated meter 300 which can perform both digital and alternate site body fluid sampling and analysis is illustrated in FIGS. 19A-19B. According to this embodiment, the integrated meter 300 generally comprises a housing 312, a catalyst device 314 in the form of an inflatable bladder or cuff 316. The cuff 316 is attached to the housing 312 in a movable manner via a hinge 318. A footprint 320 is provided on the exterior of the housing 312 which is adapted to receive a digit thereon prior to commencement of the sampling and analysis procedure. The integrated meter 300 may further comprise a disposable cartridge 331, as well as a pump 351 having both positive and negative pressure feed lines 330,332, respectively. When it is desired to use the device for digital body fluid sampling and analysis, the cuff 316 is folded upwardly to the position illustrated in FIG. 19A whereby a digit can be inserted there through and placed over the footprint 320 in a manner previously described herein. Alternatively, at the election of the user, the integrated meter 300 can be used for alternate site body fluid sampling and analysis. As illustrated in FIG. 19B, the cuff 316 can be folded back and received within a recess 334 formed in the housing 312 of the integrated meter 300. By repositioning the cuff 316 in this manner, the meter 300 can be grasped and applied to an alternate site by pressing the footprint 320 directly to the skin of the user at the desired location for alternate site body fluid sampling and analysis.

Figure 20A:
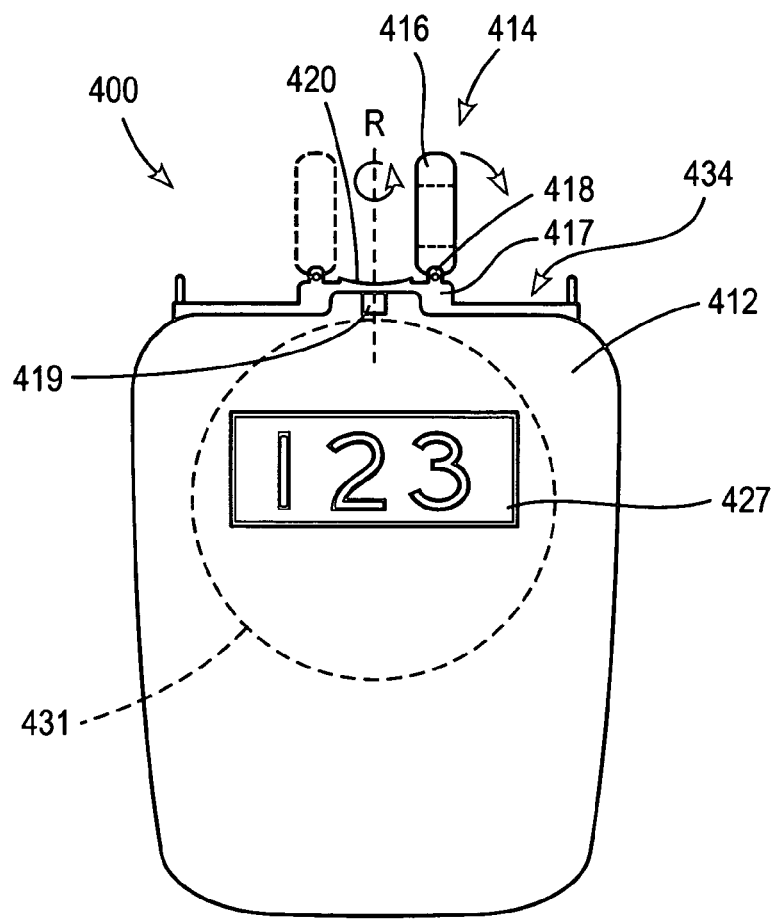
FIGS. 20A-20B are side views of an integrated device formed according to yet another alternative embodiment of the present invention.
Figure 20B:
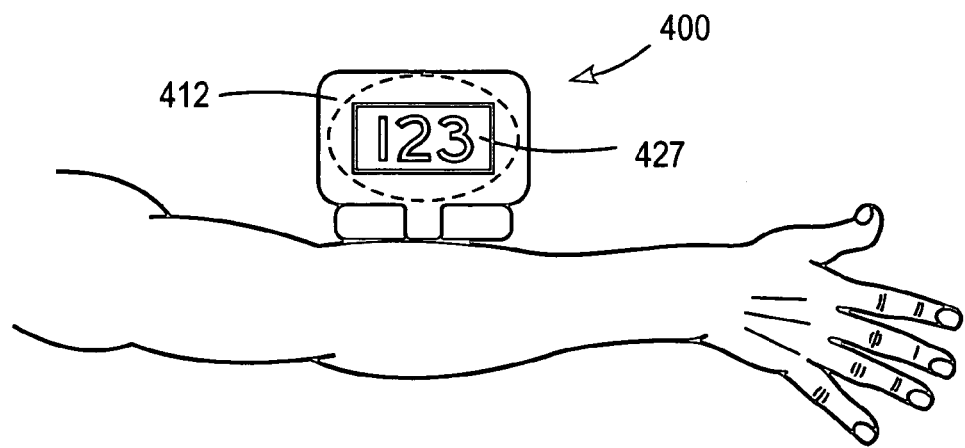

According to an alternative embodiment, an integrated meter 400 can be constructed as illustrated in FIGS. 20A-20B. The integrated meter 400 generally includes a housing 412, and a catalyst device 414, which may be in the form of an inflatable bladder or cuff 416, a display 427 and a disposable cartridge 431, all constructed as previously described herein. The cuff 416 is connected to a frame 417 via a pivotable hinge or connector 419. The footprint 420 may be connected to the frame 417, instead of directly connected to the housing 412. The frame 417 is connected to the housing 412 via a second pivotable connection 419. This the second pivotable connection 419 allows the frame 417, and the cuff 416 attached thereto, to be rotated in the manner indicated at arrow R. This pivotable connection 419 allows the cuff 416 to be repositioned on the opposite side of the device, as indicated by the broken lines appearing in FIG. 20A, thereby facilitating either right-handed or left-handed testing by the user. The cuff 416 is positioned as illustrated in FIG. 20A when it is desired to use the device for digital body fluid sampling and analysis. When it is desired to use the integrated meter 400 for alternate site body fluid stamping and analysis, the cuff 416 can be folded back and received within a recess 434 formed in the frame 427, as illustrated in FIG. 20B. Optionally, the integrated meter 400 and make include a feature which senses that the device is being used for alternate site testing (e.g., sensors that detect when the cuff 46 has been folded back and received within a recess 434), and then inverts the output on the display 417 so as to facilitate reading the results of the analysis when the integrated meter is oriented in a manner depicted in FIG. 20B.

Figure 21A:
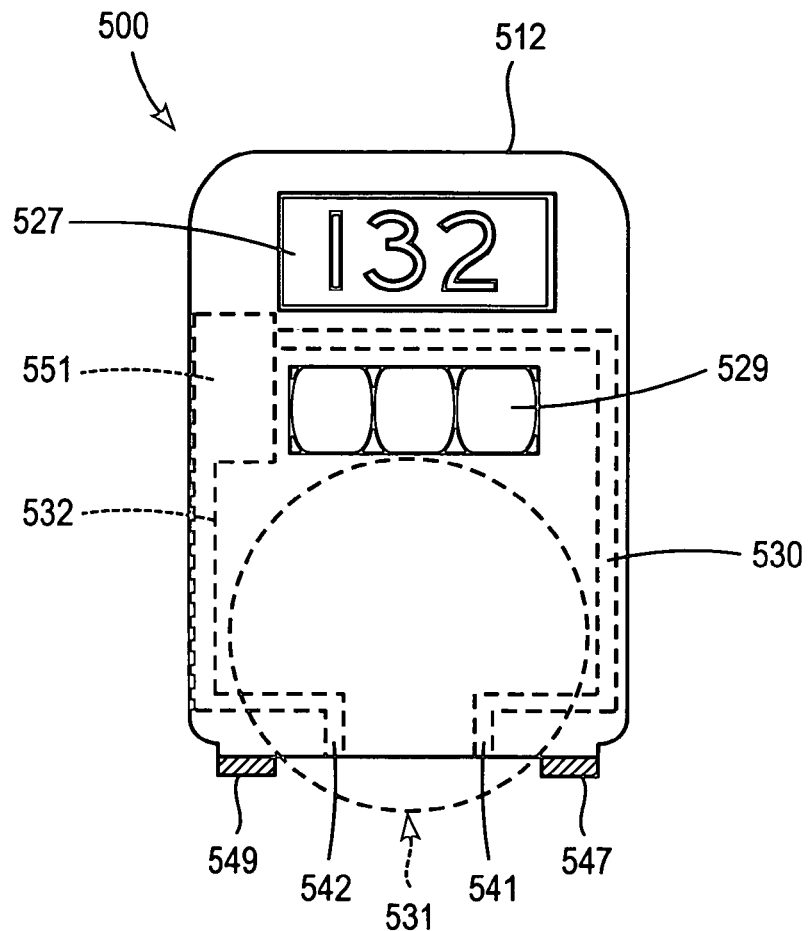
FIGS. 21A-21D are side views of still another alternative embodiment of an integrated device the present invention.
Figure 21B:
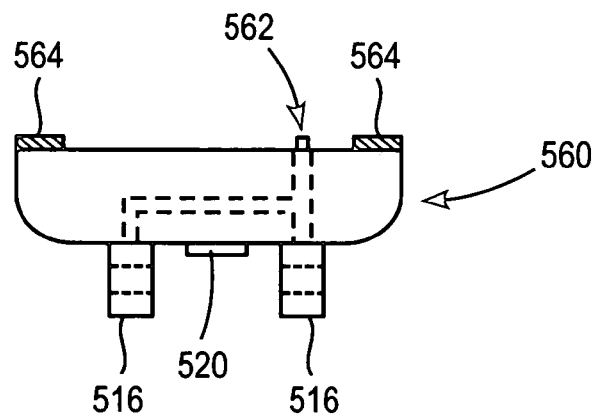
Figure 21C:
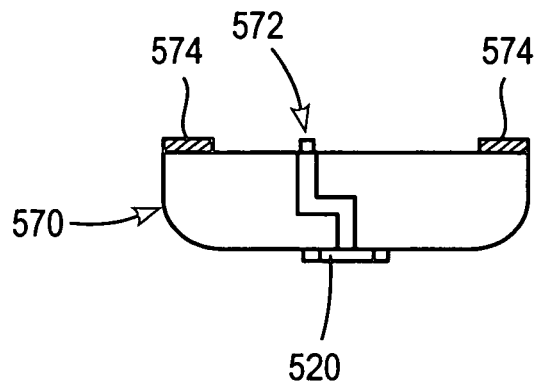

FIGS. 21A-21D illustrate a further alternative embodiment constructed according to the present invention. As illustrated therein, the integrated device 500 is composed of at least two separate components, a main component (FIG. 21A) and one or more attachments (FIGS. 21B, 21C). As illustrated, the integrated meter 500 generally comprises a housing 512, a display 527, one or more buttons 529, and a disposable cartridge 531, all constructed as previously described herein. The integrated meter 500 further comprises a pressure pump 551 which is connected to a positive feed line 530, as well as a negative pressure feed line 532. The positive pressure feed line 530 terminates in a female coupling 541. Similarly, the negative pressure feed line 532 terminates in a female coupling 542. The couplings 541 and 542 can be structured such that they are normally sealed in a closed matter until a corresponding male member is inserted therein, thereby opening the normally closed end and enabling fluid communication with the pump 551.

A first attachment 560 (FIG. 21B) is constructed to permit digital body fluid sampling and analysis. The first attachment 560 comprises a plurality of pressure cuffs 516,516' fixedly mounted thereto. This construction facilitates either right or left-handed testing. The attachment 560 further comprises a footprint 520 constructed as previously described herein. A male connector 562 is also provided which provides for fluid communication with the interior of the cuffs 516,516'. The male connector 562 is configured for insertion into corresponding female connector 541 present in the main component of the arrangement. Thus, by this construction, positive pressure can be fed from the pump and introduced into the interior of one or more of the inflatable cuffs 516,516'. In addition, or optionally, a plurality of electrical contacts 564 may also be provided on the attachment 560. These electrical contacts are configured to mate with corresponding electrical contacts 547,549 disposed on the main unit (FIG. 21A). By virtue of the nature of the electrical contacts 564, a signal is sent to the electronics contained in the integrated meter 500 that indicate that a digital sampling and analysis module is connected thereto. Based on the signal, various controls and signals can then be generated which tailor the functionality of the integrated meter 500 specifically for digital body fluid sampling and analysis. For example, a solenoid or similar device can be used to open and close valves present in one or more of the feed lines 530, 532, thereby selectively applying positive pressure to the attachment, and more specifically, to the interior of the cuffs 516,516' connected thereto.

Figure 21D:
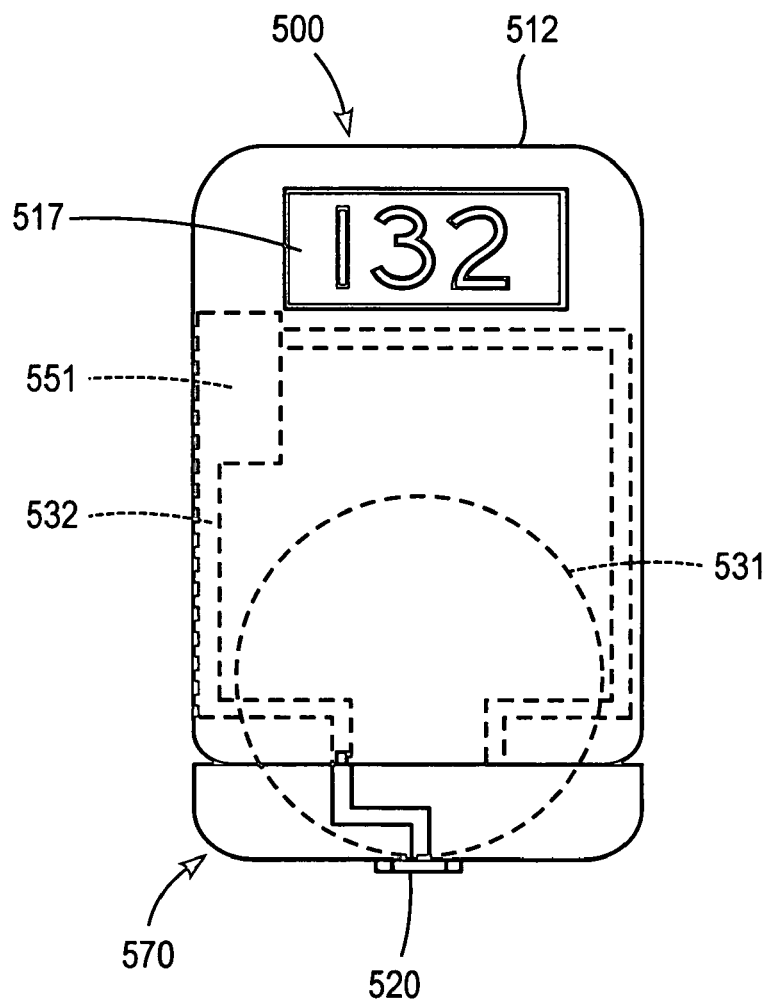

As illustrated in FIG. 21C, a second attachment 570 can be provided which is constructed for alternate site body fluid sampling and analysis. The second attachment 570 generally comprises a footprint 520 disposed on the bottom surface thereof. The second attachment 570 further comprises a male connector 572 which is configured for mating with the corresponding female connector 542 present in the main unit (FIG. 21A), thereby enabling pressure communication with the pump 551. More specifically, the connection between a male coupling 572 and a female coupling 542 enables a vacuum to be applied in the vicinity of the footprint 520 when placed against the skin of the user, thereby serving to act as a catalyst for the expression of body fluid at the sampling site. In addition, or optionally, the attachment 570 also includes one or more electrical contacts 574 which are constructed and function in a manner similar to the electrical contacts 564 described in connection with the first attachment 560. FIG. 21D illustrates an integrated meter 500 having the second attachment 570 attached thereto, thereby rendering the device suitable for alternate site body fluid sampling and analysis.

Figure 22:
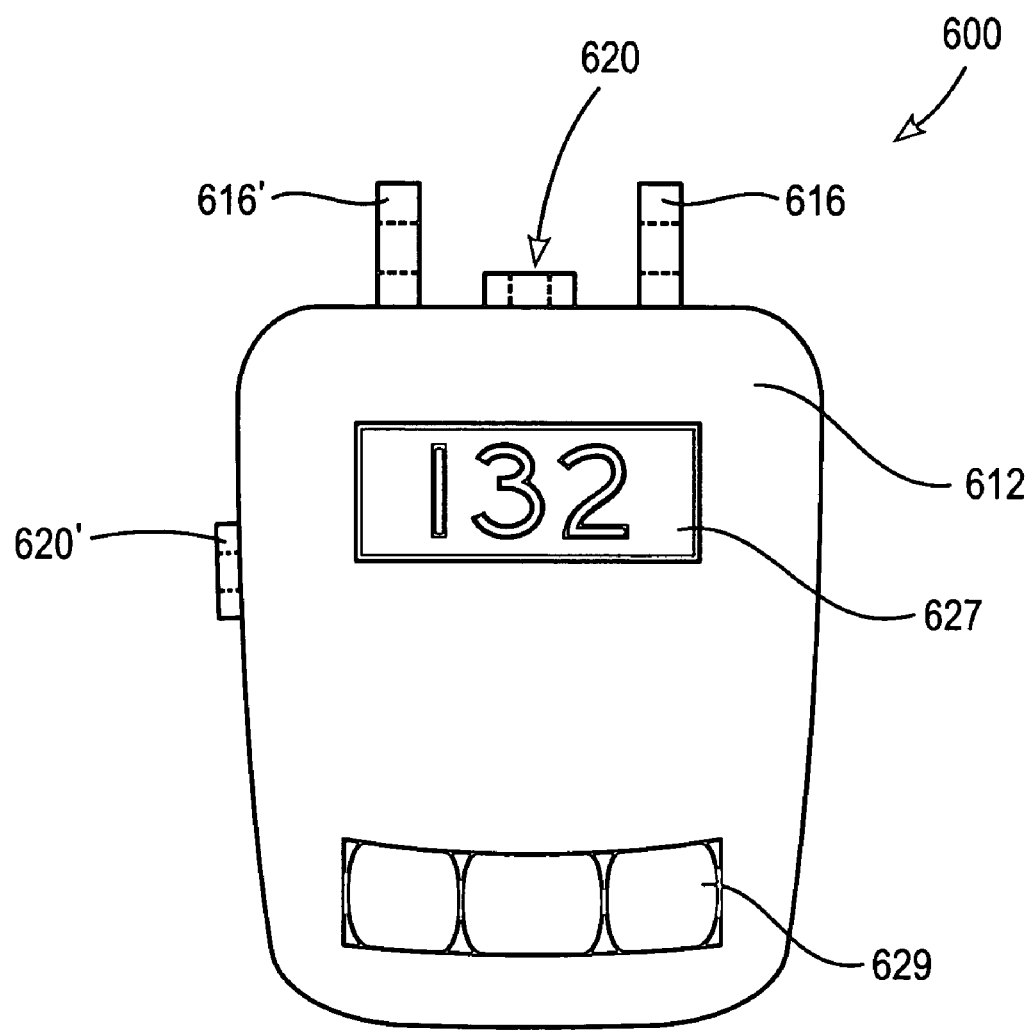
FIG. 22 is a side view of an additional embodiment of an integrated device formed according to the present invention.

According to a further alternative embodiment, an integrated meter 600 can be constructed which is capable of both digital body fluid sampling and analysis, as well as alternate site body fluid sampling and analysis, without the use of attachments. Such a construction as illustrated in FIG. 22. As illustrated therein, the integrated meter 600 generally comprises a housing 612, and one or more cuffs 616,616' securely attached thereto. This construction facilitates digital body fluid sampling and analysis from either the right or left hand of the user. The integrated meter 600 may also include a display 627 and one or more buttons 629, as well as any of the other previously described features or alternative constructions set forth previously herein. The integrated meter 600 further includes a first of footprint 620 which is provided for digital body fluid sampling and analysis. The integrated meter 600 further includes at least one additional footprint 620' which is located at a position on the integrated meter 600 which allows easy access thereto for positioning the meter 600 and sampling body fluid at an alternate site. It should be understood that the positioning of the footprints 620,620' is not limited to the arrangement depicted in the illustrated embodiment. The footprint 620 and/or footprint 620' can be disposed on any suitable face, at any suitable location, on the integrated meter 600 so long as the functionality of providing for both digital and alternate site body fluid sampling analysis can be provided.

Figure 23A:
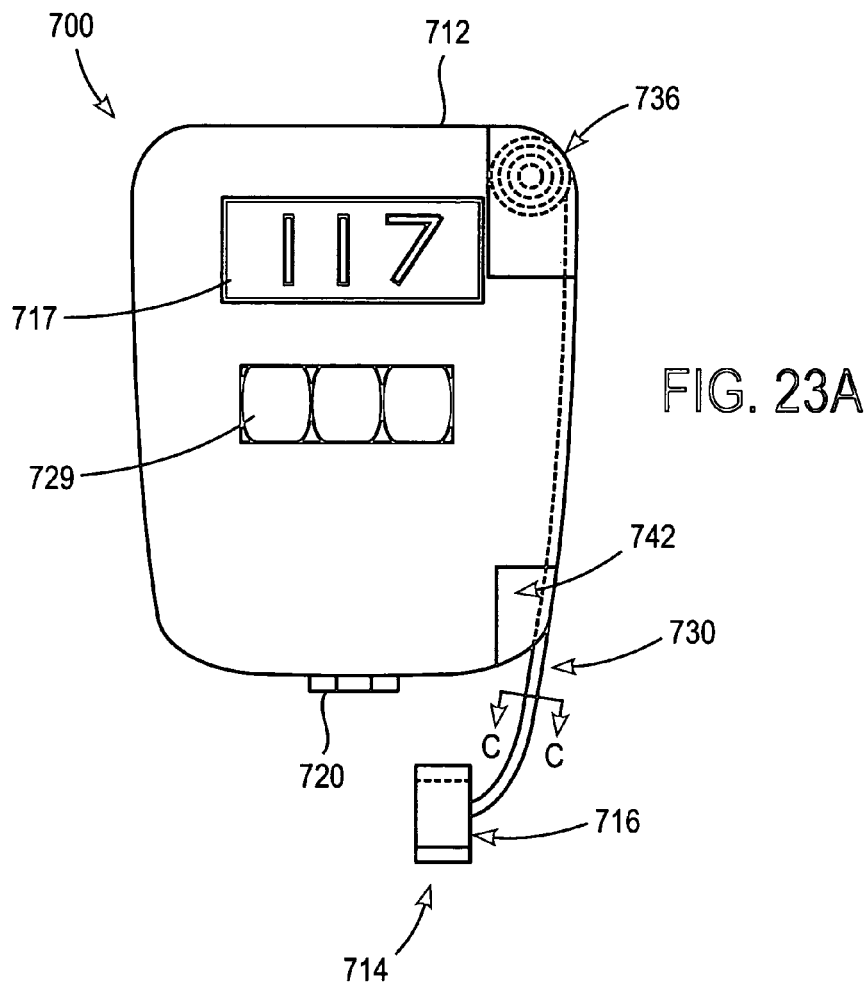
FIGS. 23A-23C are side, cross-sectional and partial side views, respectively, of an integrated device formed according to an additional alternative embodiment of the present invention.
Figure 23B:
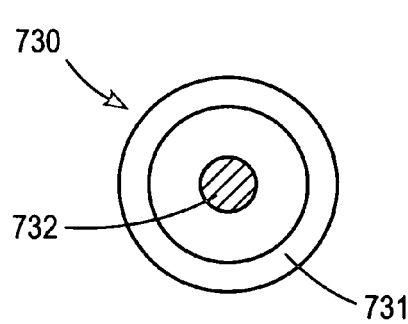
Figure 23C:
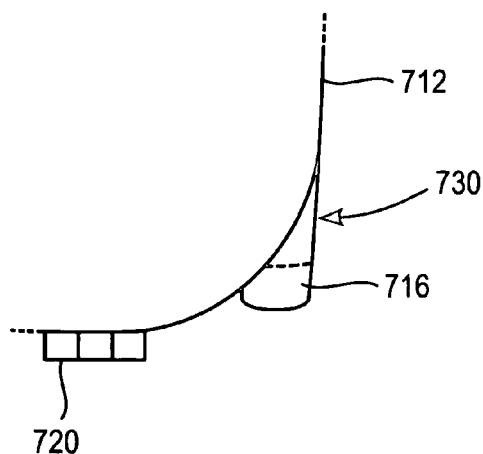

An integrated meter capable of both digital and alternate site body fluid sampling and analysis constructed according to a further alternative embodiment of the present invention is illustrated in FIGS. 23A-23C. As illustrated therein, the integrated meter 700 generally comprises a housing 712, a display 717, a footprint 720, one or more buttons 729, and a catalyst device 714 in the form of a retractable cuff 716. The cuff 716, as with the previously described embodiments, maybe formed in any suitable manner and may take any of the alternative constructions described previously. In addition, the integrated meter 700 comprise any one or more, or combinations of features previously described its association with the other embodiments. Again, as with the previously described embodiments, in the interest of conciseness, an exhaustive listing of the optional features associated with this embodiment has been omitted. The cuff 716 is tethered to the integrated meter 700 via a pressure delivery tube/cable assembly 730. As illustrated in FIG. 23B, the pressure delivery tube/cable assembly 730 generally comprises a hollow tubular member 731 which can deliver pressurized air to the cuff 716, as well as a concentrically located cable 732, which adds strength to the assembly thereby enabling retraction and removal of the cuff 716. It should be understood that the pressure to delivery tube/cable assembly 730 is not limited to the illustrated embodiment, but can take on further alternative constructions so long as the desired functionality is maintained. When pulled out into the position illustrated in FIG. 23A, a digit can be inserted through the cuff 716 and placed over the footprint 720 in a manner previously described herein, thus enabling digital body fluid sampling and analysis. When the user desires to use the integrated meter 700 for alternate site body fluid sampling and analysis, the cuff 716 can be retracted via a tensioning device 736 having a conventional construction. Upon retraction, the cuff 716 is received within a similarly shaped recess 742 which is formed in a housing 712. As illustrated in FIG. 23C, the majority of the cuff 716 is received within the recess 742, however, a small portion remains outside the recess such that it can be easily grasped by the user and withdrawn for use in digital body fluid sampling and analysis.

An exemplary body fluid sampling and analysis methodology or technique, which may be utilized in conjunction with any of the above-mentioned catalyst devices or integrated meters, but is not necessarily limited thereto, is described as follows.

A user loads a fresh disposable cartridge containing a plurality of skin penetration members and analysis sites into an integrated meter. The integrated meter then reads calibration data contained in or on the cartridge. This data can be read in any suitable manner. For example, a bar code may be placed on the cartridge which can be optically read by the optical assembly contained within the meter. The integrated meter then selects the proper lookup table or algorithm to calculate an aggregate glucose measurement taking into consideration the calibration data. The meter may then place itself in a ready mode waiting for a trigger to initiate sampling and testing. The user then either manually presses a button or trigger to initiate sampling and analysis, or the device verifies that it is properly positioned on the skin of the user and ready to begin the sampling and analysis procedure. Suitable sensors to accomplish this include optical, capacitive or pressure sensors. The device then initiates a catalyst which acts to facilitate the expression of body fluid. According to one alternative embodiment, the catalyst is an inflatable member that exerts pressure on a digit. Alternatively, the catalyst is vacuum pressure which generates suction at the sampling site. Sensors present in the meter may be used to monitor and control the positive or negative pressure of the catalyst. After achieving a target pressure for a desired period of time, the skin penetration member (e.g., a hollow needle) is actuated and driven into the skin of the user to create a wound site. The skin penetration member comes to rest in or directly on the wound created at the sampling site where it is in the desired position for collecting a sample of body fluid expressed from the wound. The integrated meter may further include a mechanism for detecting a whether a sufficient amount of sample has been expressed. Details of such suitable detection techniques are described in detail in U.S. Pat. No. 7,052,652, entitled ANALYTE CONCENTRATION DETECTION DEVICES AND METHODS, the entire content of which is incorporated herein by reference. Once the desired amount of body fluid has been obtained, the catalyst is deactivated. A sample of body fluid is in fluid communication with a device or mechanism which creates a detectable signal upon reaction within analyte present in the sample body fluid. For example, one such suitable mechanism is a absorbent pad containing a chemical reagent which, upon reaction with the analyte produces a reaction spot which can be optically detected. An optical assembly which is an optical communication with the above described signal generating mechanism is utilized to detect the signal created via reaction with the analyte and communicate the signals to supporting electronics contained within the meter. The concentration of a target analyte (e.g., glucose) can then be calculated using these signals as a basis. Additional factors may be considered during these calculations, such as the sample size, levels of other substances contained in the sample (e.g. hematocrit), etc. Such optional calculation techniques are described in further detail in U.S. patent application Ser. No. 11/239,122, entitled ANALYTE DETECTION DEVICES AND METHODS WITH HEMATOCRIT/VOLUME CORRECTION AD FEEDBACK CONTROL, the entire content of which is incorporated herein by reference. These calculations quantify the amount of analyte contained in the sample body fluid. This quantity is displayed on a suitable display contained within the meter which can be easily read by the user. The integrated meter then automatically indexes the disposable cartridge to present a fresh unused skin penetration member which will be utilized to perform the next sampling and analysis event.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. §112, 16, unless the term "means" is explicitly used.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. An integrated device, the device comprising:
a device housing;
at least one skin-penetration member in the device housing;
a catalyst member constructed for application of circumferential pressure proximate to a sampling site; and
a pump;
wherein the catalyst member is pivotably connected to the device housing in a manner such that the catalyst member can pivot relative to and away from the device housing between a first position and a second position; and
wherein the catalyst member comprises a connection with the device housing such that the pump applies a positive pressure to the catalyst member when the catalyst member is in the second position, wherein the device is configured to perform a first fluid sampling procedure when the catalyst member is in the first position and is further configured to perform a second fluid sampling procedure when the catalyst member is in the second position, wherein the catalyst member applies circumferential pressure to the sampling site during the second fluid sampling procedure, wherein the pump is configured to supply positive pressure to the catalyst member during the second fluid sampling procedure, and wherein the pump can be switched to alternatively supply negative pressure to the sampling site during the first fluid sampling procedure.

2. The device of claim 1, wherein the housing contains the at least one skin-penetration member, a mechanism for transporting a sample of body fluid to an analysis site, and an arrangement for quantifying an amount of analyte contained in the sample of body fluid, and a device for communicating the amount of analyte contained in the sample of body fluid.

3. The device of claim 2, wherein the arrangement for quantifying the amount of analyte contained in the sample of body fluid comprises at least one complementary metal oxide semiconductor (CMOS)-based detector element.

4. The device of claim 3, wherein the arrangement for quantifying the amount of analyte contained in the sample of body fluid comprises a linear array of complementary metal oxide semiconductor (CMOS)-based detector elements.

5. The device of claim 1, further comprising a footprint, wherein the footprint is disposed on the housing or an attachment to the housing, and is constructed to be applied to the sampling site on the skin of a user.

6. The device of claim 5, wherein the footprint comprises an elastomer.

7. The device of claim 5, wherein the catalyst member and the footprint are separate elements.

8. The device of claim 1, wherein the catalyst member comprises a cuff constructed to apply circumferential pressure to a digit placed therein.

9. The device of claim 8, wherein the cuff is inflated by the pump.

10. The device of claim 8, wherein the cuff is circumferentially continuous.

11. The device of claim 1, wherein the at least one skin-penetration member comprises a needle.

12. The device of claim 1, further comprising a footprint disposed on the housing constructed to be applied to the sampling site on the skin of a user during body fluid sampling.

13. The device of claim 1, wherein the housing contains a disposable cartridge comprising a plurality of skin-penetration elements and analysis sites, such that multiple tests can be performed without replacing the cartridge.

14. The device of claim 13, wherein the cartridge is moveable in order to present a new skin-penetration element and analysis site for use after performance of a preceding sampling event.

15. The device of claim 14, wherein the device is constructed such that a plurality of skin-penetration members and analysis sites are presented for possible body fluid sampling in a manner that permits either digital or alternate-site sampling, as elected by a user.

16. The device of claim 1, wherein the catalyst member is connected to the housing via a hinge.

17. The device of claim 1, further comprising at least one sensor configured and arranged to detect a presence of the skin of the user, wherein upon said detection the device automatically activates the catalyst member, and drives the at least one skin-penetration member into the skin of the user.

18. The device of claim 1, wherein the catalyst member is connected to the housing such that in the first position the catalyst member is disposed a first distance from the housing, and when pivoted away from the housing is disposed in the second position at a second distance away from the housing, wherein the second distance is greater than the first distance.

19. The device of claim 18, further comprising a recess disposed in the housing, and wherein in the first position the catalyst member is disposed within the recess, and in the second position the catalyst member is located outside of the recess.

20. The device of claim 1, wherein the catalyst member comprises a passage therethrough constructed and arranged to receive an outer periphery of a digit therein, while leaving a tip of the digit exposed.

21. The device of claim 1, further comprising a cartridge received within the housing, the cartridge comprising a plurality of skin penetration members and a plurality of analysis sites.

22. An integrated device, the integrated device comprising:
a housing;
at least one skin-penetrating member in the housing;
a catalyst member constructed for the application of circumferential pressure proximate to a sampling site; and
a pump constructed and arranged to supply positive pressure to the catalyst member and negative pressure to the sampling site;
wherein the catalyst member is pivotably connected to the housing in a manner such that the catalyst member can pivot relative to and away from the housing between a first position and a second position,
wherein the device is configured to perform a first fluid sampling procedure when the catalyst member is in the first position and is further configured to perform a second fluid sampling procedure when the catalyst member is in the second position, wherein the catalyst member applies circumferential pressure to the sampling site during the fluid second sampling procedure, wherein the pump is configured to supply positive pressure to the catalyst member during the second fluid sampling procedure, and wherein the pump can be switched to alternatively supply negative pressure to the sampling site during the first fluid sampling procedure.

23. An integrated device, the device comprising:
a housing;
a footprint disposed on the housing or as an attachment to the housing;
a cartridge received within the housing, the cartridge comprising a plurality of skin-penetration members and a plurality of analysis sites;
a catalyst member pivotably connected to the housing and constructed for application of pressure proximate to a sampling site, wherein the catalyst member is pivotable relative to the housing between a first position and a second position, the second position allowing a tip of a digit received within the catalyst member to be placed upon the footprint; and
a pump constructed and arranged to supply positive pressure to the catalyst member and negative pressure to the sampling site,
wherein the device is configured to perform a first fluid sampling procedure when the catalyst member is in the first position and is further configured to perform a second fluid sampling procedure when the catalyst member is in the second position, wherein the catalyst member applies circumferential pressure to the sampling site during the second fluid sampling procedure, wherein the pump is configured to supply positive pressure to the catalyst member during the second fluid sampling procedure, and wherein the pump can be switched to alternatively supply negative pressure to the sampling site during the first fluid sampling procedure.

24. The device of claim 23, wherein the catalyst member comprises a cuff constructed to apply circumferential pressure to a digit placed therein.

25. The device of claim 24, wherein the cuff is inflated by the pump contained in the housing or in the catalyst member.

26. The device of claim 23, wherein the cartridge is moveable in order to present a new skin-penetration element and analysis site for use after performance of a preceding sampling event.

27. The device of claim 23, wherein the catalyst member is connected to the housing via a hinge.

28. The device of claim 23, further comprising a recess disposed in the housing, and wherein in the first position the catalyst member is disposed within the recess, and in the second position the catalyst member is located outside of the recess.

29. The device of claim 23, wherein the catalyst member is circumferentially continuous.

30. The device of claim 23, wherein the catalyst member comprises a passage therethrough constructed and arranged to receive an outer periphery of a digit therein, while leaving a tip of the digit exposed.

31. The device of claim 23, wherein the catalyst member and the footprint are separate elements.

32. An integrated device for body fluid sampling and analysis of alternative sites and digital sites, at election of a user, the device comprising:
- a housing;
- a footprint disposed on the housing or as an attachment to the housing;
- a cartridge received within the housing, the cartridge comprising a plurality of skin-penetration members and a plurality of analysis sites;
- a catalyst member pivotably connected to the housing and constructed for application of pressure proximate to a sampling site, wherein the catalyst member is movable relative to the housing between a first position and a second position, the first position allowing placement of the footprint on an alternative site, and the second position allowing a tip of a digit received within the catalyst member to be placed upon the footprint; and
- a pump constructed and arranged to supply positive pressure to the catalyst member and negative pressure to the sampling site,
- wherein the device is configured to perform a first fluid sampling procedure when the catalyst member is in the first position and is further configured to perform a second fluid sampling procedure when the catalyst member is in the second position, wherein the catalyst member applies circumferential pressure to the sampling site during the second fluid sampling procedure, wherein the pump is configured to supply positive pressure to the catalyst member during the second fluid sampling procedure, and wherein the pump can be switched to alternatively supply negative pressure to the sampling site during the first fluid sampling procedure.

33. The integrated device of claim 32 wherein the housing comprises a recess, and wherein the catalyst member is received within the recess in the first position.

34. The integrated device of claim 33, wherein the catalyst member is outside the recess when in the second position.

35. The integrated device of claim 34, wherein the housing comprises a top surface and at least one side surface, and wherein the recess is disposed in the at least one side surface of the housing.

36. The integrated device of claim 35, wherein the catalyst member comprises an inflatable cuff.

37. The integrated device of claim 32, further comprising a positive pressure feed line between the pump and a member, and a negative pressure feed line between the pump and the footprint.

38. The integrated device of claim 32, wherein each of the plurality of skin-penetration members is attached to a hub, and the hub is operably associated with a spring for driving the skin-penetration member into a skin surface of a user.

39. The integrated device of claim 38, wherein the spring comprises a torsional spring.

* * * * *